US010827223B2

(12) United States Patent
Frusina et al.

(10) Patent No.: US 10,827,223 B2
(45) Date of Patent: *Nov. 3, 2020

(54) SYSTEMS AND METHODS FOR TRANSMISSION OF DATA STREAMS

(71) Applicant: DEJERO LABS INC., Waterloo (CA)

(72) Inventors: Bogdan Frusina, Kitchener (CA); Barry Gilhuly, Waterloo (CA); Arif Hudda, Kitchener (CA); Cameron Kenneth Smith, Oakville (CA); Anthony Todd Schneider, Waterloo (CA); David Pui Keung Sze, Waterloo (CA)

(73) Assignee: DEJERO LABS INC., Waterloo (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/366,510

(22) Filed: Mar. 27, 2019

(65) Prior Publication Data
US 2019/0222897 A1 Jul. 18, 2019

Related U.S. Application Data

(63) Continuation of application No. 15/683,405, filed on Aug. 22, 2017, now Pat. No. 10,284,912, which is a
(Continued)

(51) Int. Cl.
*H04N 21/462* (2011.01)
*H04N 21/278* (2011.01)
(Continued)

(52) U.S. Cl.
CPC ..... *H04N 21/4621* (2013.01); *H04N 21/2187* (2013.01); *H04N 21/2343* (2013.01);
(Continued)

(58) Field of Classification Search
None
See application file for complete search history.

(56) References Cited

U.S. PATENT DOCUMENTS 10,284,912 B2 * 5/2019 Frusina .............. H04N 21/4621

OTHER PUBLICATIONS

Form PTO/SB/08a filed in related U.S. Appl. No. 14/329,112, dated May 22, 2017.
(Continued)

*Primary Examiner* — Mulugeta Mengesha
*Assistant Examiner* — Charles N Hicks
(74) *Attorney, Agent, or Firm* — Norton Rose Fulbright Canada LLP

(57) ABSTRACT

Systems and methods for real-time transmission of data streams are disclosed. A controller receives data representing selected stream parameters from a browser residing on a computing device. The controller transmits the received data to a video transmitting device. A transcoder receives a first data stream generated according to the selected stream parameters from the video transmitting device. The transcoder generates a second data stream from the first data stream, the second data stream formatted for browser display; and then transmits the second data stream to the browser. A user may remotely control the video transmitting device using the browser. A user may view data streams from multiple video transmitting devices using the browser.

30 Claims, 9 Drawing Sheets

Related U.S. Application Data continuation of application No. 14/329,112, filed on Jul. 11, 2014, now Pat. No. 9,769,527.

(60) Provisional application No. 61/845,195, filed on Jul. 11, 2013.

(51) Int. Cl.

| | |
|---|---|
| *H04N 21/2365* | (2011.01) |
| *H04N 21/2343* | (2011.01) |
| *H04N 21/24* | (2011.01) |
| *H04N 21/4782* | (2011.01) |
| *H04N 21/61* | (2011.01) |
| *H04N 21/6373* | (2011.01) |
| *H04N 21/647* | (2011.01) |
| *H04N 21/2187* | (2011.01) |
| *H04N 21/6583* | (2011.01) |

(52) U.S. Cl.
CPC ............ *H04N 21/23655* (2013.01); *H04N 21/234363* (2013.01); *H04N 21/234381* (2013.01); *H04N 21/2405* (2013.01); *H04N 21/278* (2013.01); *H04N 21/4782* (2013.01); *H04N 21/6125* (2013.01); *H04N 21/6175* (2013.01); *H04N 21/6373* (2013.01); *H04N 21/64761* (2013.01); *H04N 21/6583* (2013.01)

(56) References Cited

OTHER PUBLICATIONS

Form PTO/SB/08a filed in related U.S. Appl. No. 14/329,112, dated Jan. 11, 207.
Form PTO-892 filed in related U.S. Appl. No. 14/329,112, dated Jan. 5, 2017.
Form PTO-892 filed in related U.S. Appl. No. 14/329,112, dated Jun. 15, 2016.
Form PTO-892 filed in related U.S. Appl. No. 14/329,112, dated Nov. 19, 2015.
Form PTO-892 filed in related U.S. Appl. No. 14/329,112, dated May 15, 2015.
Form PTO/SB/08a filed in related U.S. Appl. No. 14/329,112, dated May 15, 2015.
Form PTO/SB/08a filed in related U.S. Appl. No. 14/329,112, dated Nov. 10, 2014.
Form PTO/SB/08a filed in related U.S. Appl. No. 15/683,405, dated Sep. 25, 2018.
Form PTO-892 filed in related U.S. Appl. No. 15/683,405, dated May 17, 2018.
Form PTO/SB/08a filed in related U.S. Appl. No. 15/683,405, dated May 17, 2018.

* cited by examiner

K grows beyond X (X=4) and framerate is decreased by integer multiples to compensate K shrinks beyond X (X=4) and framerate is increased by integer multiples to compensate

SYSTEMS AND METHODS FOR TRANSMISSION OF DATA STREAMS

CROSS-REFERENCE TO RELATED APPLICATIONS

This application is a continuation of U.S. application Ser. No. 15/683405, filed Aug. 22, 2017, which is a continuation of U.S. application Ser. No. 14/329,112 filed on Jul. 11, 2014, entitled SYSTEMS AND METHODS FOR TRANSMISSION OF DATA STREAMS, which claims the benefit of U.S. Provisional Patent Application No. 61/845,195, filed Jul. 11, 2013, the contents of U.S. application Ser. No. 15/683,405, U.S. application Ser. No. 14/329,112 and U.S. Provisional Patent Application No. 61/845,195 are hereby incorporated by reference in their entireties.

FIELD

Embodiments described herein relate to systems and methods for transmission of data streams, and in particular, to systems and methods for real-time management and transmission of video and audio data streams over networks.

BACKGROUND

The use of video and audio content is growing, such as for example, live video and video that are provided or generated by traditional viewers (so-called user generated content or UGC). Usage of mobile video encoders/transmitters over cellular (including bonded cellular) and other mobile connection types (WiFi, microwave, etc.) networks is also growing.

Many readily available mobile computing devices (e.g., smart phones, tablets) have sufficient computing capability and wireless transmission performance to deliver good quality video at low latency for live broadcast.

Content providers (e.g., television stations and websites) may wish to encourage viewers (e.g. users) to send in their content for further distribution and broadcast.

In consideration of these factors, more live video and audio content may be delivered, which increases the need for management, transmission, switching, and routing of video and audio content.

Thus, there exists a need for an improved, easy to use system that will allow collection, selection and management of large volumes of live, real-time, or near real-time video and audio content for users and broadcasters, or at least a useful alternative.

SUMMARY

In an aspect, there is provided a system for real-time transmission of data streams. The system includes a controller coupled to a browser residing on a computing device and a video transmitting device adapted to generate and transmit a first data stream comprising at least one of video data and audio data. The controller is adapted to receive, from the browser, data representing selected stream parameters; and to transmit the received data to the video transmitting device. The system also includes a transcoder coupled to the browser and the video transmitting device. The transcoder is adapted to receive, from the video transmitting device, the first data stream generated according to the selected stream parameters; to generate a second data stream from the first data stream, the second data stream formatted for browser display, and to transmit the second data stream to the browser.

The transcoder may generate the second data stream by transcoding the first data stream.

The second data stream may comprise a sequence of image files.

The second data stream may be transcoded to have a higher data rate than the first data stream.

The second data stream may include data reflective of at least one of network performance, status of the video transmitting device, and location of the video transmitting device.

The selected stream parameters may include at least one of a framerate, a resolution, and a data rate.

The transcoder may be coupled to the browser and to the video transmitting device by way of a network.

The transcoder may be adapted to receive control data from the browser and transmit the control data to the video transmitting device to remotely control the video transmitting device.

The controller may be adapted to receive control data from the browser and transmits the control data to the video transmitting device to remotely control the video transmitting device.

The system may further include a video output device coupled to the video transmitting device, the video output device adapted to receive, from the video transmitting device, a third data stream.

The third data stream may be a full-rate data stream.

The third data stream may have a higher data rate than the first data stream.

The third data stream may be shifted in time relative to the first data stream.

The video transmitting device may be a first video transmitting device, and the controller may be further coupled to a plurality of video transmitting devices including the first transmitting device.

The transcoder may be adapted to receive a data stream from each of at least two video transmitting devices of the plurality of video transmitting devices, and to transmit the received data streams to the browser.

The controller may be adapted to receive data reflecting a selection of one of the data streams.

The transcoder may be a first transcoder, and the system may further include a plurality of transcoders including the first transcoder.

The controller may be adapted to receive, from the browser, data reflecting a selection of one of the plurality of transcoders.

The number of transcoders of the plurality of transcoders may be dynamically adjustable based on demand.

The controller may be adapted to transmit messages to the video transmitting device.

The messages may include at least one of interruptible fold back messages and text messages.

The transcoder may be adapted to transmit a data stream comprising video data to the video transmitting device.

The data stream transmitted by the transcoder to the video transmitting device may be a return video stream.

In another aspect, there is provided a method for real-time transmission of data streams. The method includes: receiving, by a controller from a browser residing on a computing device, data representing selected stream parameters; transmitting, by the controller to a video transmitting device, the received data; receiving, by a transcoder from the video transmitting device, a first data stream generated according to the selected stream parameters; generating, by the transcoder, a second data stream from the first data stream, the second data stream formatted for browser display; and transmitting, by the transcoder to the browser, the second data stream.

The method may further include remotely controlling the video transmitting device from the browser, including receiving by the transcoder from the browser, control data, and transmitting, by the transcoder to the video transmitting device, the control data.

The method may further include remotely controlling the video transmitting device from the browser, including receiving, by the controller from the browser, control data; and transmitting, by the controller to the video transmitting device, the control data.

The method may further include automatically adjusting, at the transcoder, a framerate of the second data stream based on feedback data reflecting a number of frames transmitted and a number of frames for which acknowledgement is received.

The method may further include receiving, by a video output device, a third data stream.

The third data stream may be a full-rate data stream.

The third data stream may have a higher data rate than the first data stream.

In a further aspect, there is provided a computer-readable storage medium storing one or more sequences of instructions which, when executed by one or more processors, causes the one or more processors to perform a method for real-time transmission of data streams, the method comprising: receiving, by a controller from a browser residing on a computing device, data representing selected stream parameters; transmitting, by the controller to a video transmitting device, the received data; receiving, by a transcoder from the video transmitting device, a first data stream generated according to the selected stream parameters; generating, by the transcoder, a second data stream from the first data stream, the second data stream formatted for browser display; and transmitting, by the transcoder to the browser, the second data stream.

Other aspects and features of the present invention will become apparent to those of ordinary skill in the art upon review of the following description of specific embodiments of the invention in conjunction with the accompanying figures.

DRAWINGS

Various embodiments will now be described, by way of example only, with reference to the following drawings, in which.

Figure 8:
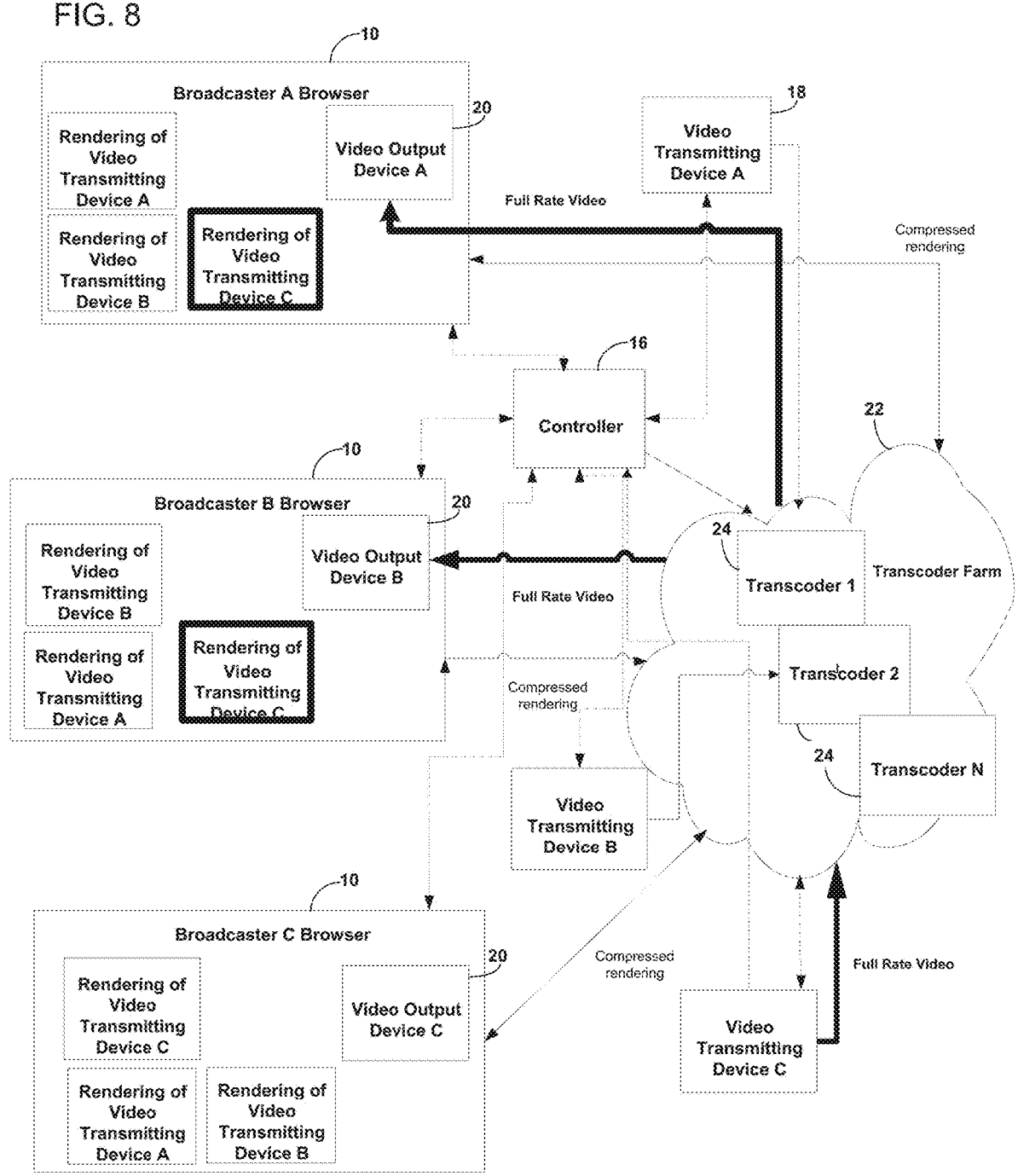
Figure 9:
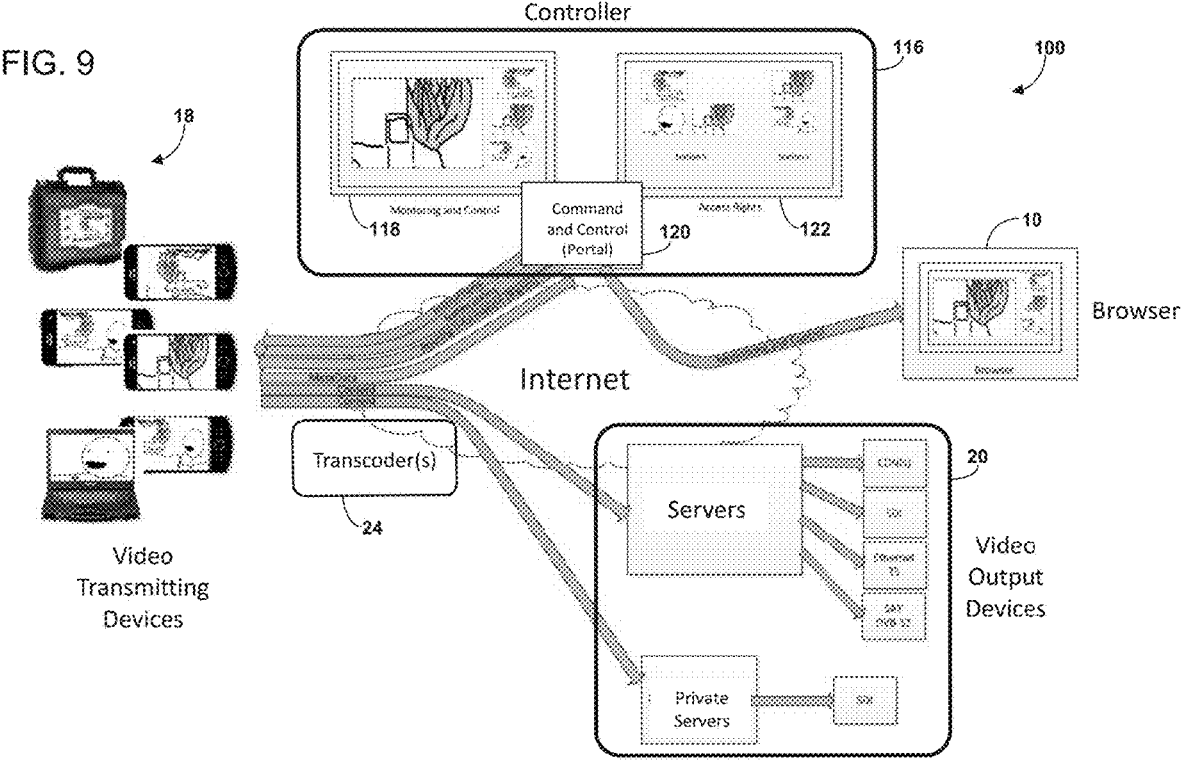

FIG. 8 is a schematic diagram of various components of a system for transmission of video data streams and a high-level description of data passed between components in the context multi-viewer and remote control functions to create a multipoint video distribution system in the cloud, according to an example embodiment; and FIG. 9 is another schematic diagram of various components of a system for transmission of video data streams, according to an example embodiment.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, the embodiments described herein may be practiced without these specific details. In other instances, well-known methods, procedures and components have not been described in detail so as not to obscure the embodiments generally described herein.

DESCRIPTION OF VARIOUS EMBODIMENTS

Systems and methods for real-time transmission of data streams are provided.

According to an example embodiment, there is provided a system that includes a controller coupled to a browser residing on a computing device and a video transmitting device adapted to generate and transmit a data stream comprising video data. The controller is adapted to receive, from the browser, data representing selected stream parameters; and to transmit the received data to the video transmitting device. The system also includes a transcoder coupled to the browser and the video transmitting device. The transcoder is adapted to receive, from the video transmitting device, a first data stream generated according to the selected stream parameters; to generate a second data stream from the first data stream, the second data stream formatted for browser display, and to transmit the second data stream to the browser.

According to another example embodiment, there is provided a method for real-time transmission of data streams. The method includes: receiving, by a controller from a browser residing on a computing device, data representing selected stream parameters; transmitting, by the controller to a video transmitting device, the received data; receiving, by a transcoder from the video transmitting device, a first data stream generated according to the selected stream parameters; generating, by the transcoder, a second data stream from the first data stream, the second data stream formatted for browser display; and transmitting, by the transcoder to the browser, the second data stream.

Some embodiments described herein may provide real-time transmission of high quality, low latency video data streams over bonded network connections or a single connection using a mobile transmitter. Bonded connections may be adaptively bonded as in U.S. application Ser. No. 12/499,151 filed Jul. 8, 2009, the entire contents of which is hereby incorporated by reference.

Further embodiments described herein may provide for management of live video and audio data streams in a cloud computing configuration using IP, with low latency video routing and switching in a cloud-based system (e.g. video and audio over IP) using a multi-viewer that incorporates remote control of video transmitting devices.

Real time remote control of one or more transmitters over a bonded connection, adaptively bonded or single connection via a web browser or native application.

Further embodiments described herein may provide for distributed video processing to address mobile transmitters that have low computing capability.

Some embodiments described herein may provide for content selection and management via a multi-viewer system incorporating pay per use, subscription, or other compensation scheme.

Further embodiments described herein may provide low latency multipoint distribution of video streams in the cloud based system using a manually or automatically scalable architecture where cloud computing resources (memory, CPU and/or network bandwidth) are manually or automatically scalable based on the demand for the services provided by the system. The system may monitor resource usage and the number of access points and scale cloud computing resources accordingly to provide dynamic scalability.

Embodiments described herein may provide improved, easy to use systems and methods that enable collection, selection and management of large volumes of live, real-time, or near real-time video and audio content for users and broadcasters, or at least useful alternatives. Some embodiments described herein may provide a system with, for example, improved latency, switching time, video resolution, perceived video quality, cost, and ease of use, and other technical features.

Embodiments described herein may provide improved systems and methods for selecting video and audio content, such as in situations where there may be a large amount of content streams delivered simultaneously. Some video recorded events may result in a large number of live video and audio data streams arriving simultaneously at a destination, such as a central control room of a service provider. The amount of content may increase if the video data streams include UGC. In video transmission applications, it may be necessary for a central control room to both modify settings of a remotely located transmitter. It may also be necessary for a central control room to see what video frames or shots of the video data stream are available from multiple transmitters so that they can select that one or more video data streams to convert to live broadcast. In some embodiments, the improved systems and methods may provide a multi-viewer, remote control of transmitters, fast switching, low latency, and the like.

Embodiments described herein may provide improved systems and methods for controlling the quality of video and audio content. Some users (e.g. video and audio content generators) are not skilled at using live video transmission technology; nor at shooting live video as required for live broadcast. It may be necessary for a centrally-located engineer to manage settings (such as latency or resolution as non-limiting examples) on a transmitter (e.g. a video transmitting device) remotely, as the on-site camera crew or user may lack the expertise to transmit video in non-standard situations (e.g. poor connectivity). In some embodiments, the improved systems and methods may provide remote control of settings and transmitters. In some embodiments, the improved systems and methods may provide bonded or adaptively bonded connections between recipients and transmitters. In some embodiments, the improved systems and methods may provide fast switching by selecting high quality paths and switching mechanisms. In some embodiments, the improved systems and methods may provide health and quality monitoring on the video and audio data stream, via overlays in a cloud-based system, for example. In some embodiments, the improved systems and methods may provide return communication between recipients and transmitters (e.g. interruptible fold back (IFB), text, chat, return video, or other data feed). In the case of return video, the transcoder(s) may be used to take video from the studio and convert it to a format that can be displayed on a user's smart phone (which may also serve as a video transmitting device) or other video transmitting device. Using this approach, the same infrastructure that is used to generate the preview stream can also be used to generate return video.

Embodiments described herein may provide improved systems and methods for compensating users for content. Users (viewers) providing UGC or other video and audio content may want to be compensated for their delivery of content. In some embodiments, the improved systems and methods may provide supported payment mechanisms and a user scoring or rating system, including searching and selecting streams based on scoring and rating.

Embodiments described herein may provide improved systems and methods for managing network and computing resource limitations. Managing a large number of simultaneous audio and video data streams may exceed the capability of network and computing infrastructure in a studio. For example, the control room may be on a limited bandwidth connection to the Internet, and may have many transmitters to control and monitor in a multi-viewer scenario. It may be important to manage bandwidth usage so as to avoid a network bottleneck from preventing full rate video from arriving to the station in a timely manner.

In an instance such as a planned sporting event, the broadcaster may have a control room on site (or in a vehicle close by, for example) to manage the various shots through a local switcher, and send a complete package back to the station for broadcast to minimize costs associated with transmission. This may not be practical in a breaking news or emergency situation, or in a situation where multiple camera crews are at materially different locations related to the same breaking news event.

At a news event (or emergency or battle scene), a control room may have multiple cameras to choose from, but limited bandwidth such that they are unable to transmit full rate (high quality) video streams over an IP network. Embodiments described herein may provide improved systems and methods for managing these example network and computing resource limitations. Both of these situations (planned sporting event and news event) are examples where cloud computing resources (memory, CPU and/or network bandwidth) which may be manually or automatically scalable based on the demand for the services provided by the system provide benefit.

In some embodiments, the improved systems and methods may send low bandwidth data stream to a cloud computing server, the studio or other recipient. In some embodiments, the improved systems and methods may implement a low bit rate transcode in a cloud based system (e.g. Scalable Vectors Graphics (SVG) of a user interface (UI), H.264 advanced video coding of bitmaps, state information and build display transmission). In some embodiments, the improved systems and methods may enable scalable cloud computing. In some embodiments, the improved systems and methods may provide distributed video encoding. For example, using transmitters in the field to provide transcoding or other functions under control of a cloud computing server.

Embodiments described herein may provide improved systems and methods for managing video encoder and transmitter resource limitations. Some video encoders and transmitters may have insufficient computing capability to support the simultaneous transmission of a full rate audio/video stream and a secondary stream that contains status information and a video preview, for example.

Also, a transmitter in a remote location sending full quality audio and video to another location in bandwidth challenged conditions (e.g. cell networks, limited Internet connection) may need to send status information and video preview data to another location (such as a control room in a central broadcast location).

Additionally, transmitters with limited computing or transmitting capability (e.g. an iPhone, tablet, laptop, or the like) may need to offload some of the computing and transmitting work elsewhere. The transmitters may be limited to sending low bitrate renderings of the UI and video preview or by sending state information and creating a virtual UI in a cloud computing server or at the central control room.

In some embodiments, the improved systems and methods may provide remotely switched transmission resolution and bit rate. In some embodiments, the improved systems and methods may perform transcoding and/or overlay of the user interface, health monitoring, performance statistics or similar using a cloud computing server or local server.

Embodiments described herein may provide improved systems and methods for authenticating video and audio content, and transmitters. Television stations and other service providers receiving content may need a way to authenticate the content and/or transmitter so they feel confident putting it up for live broadcast. For instance, the broadcaster may want to ensure that the video is being sent from the location being asserted by the person generating the content. In some embodiments, the improved systems and methods may provide per transmitter or other device licensing, geolocation based authentication, time of event authentication, user scoring or rating, and the like.

Embodiments described herein may provide improved systems and methods for sharing video and audio content. Broadcasters or other service providers may want to share the live video and audio content (e.g., UGC) they collect with other broadcasters or affiliates. They may be compensated for the content they share.

Embodiments described herein may provide a scalable cloud-based audio/video system that supports remote control, multi viewing at adjustable bitrates and resolutions and multipoint distribution along with user authentication and payment.

Figure 1:
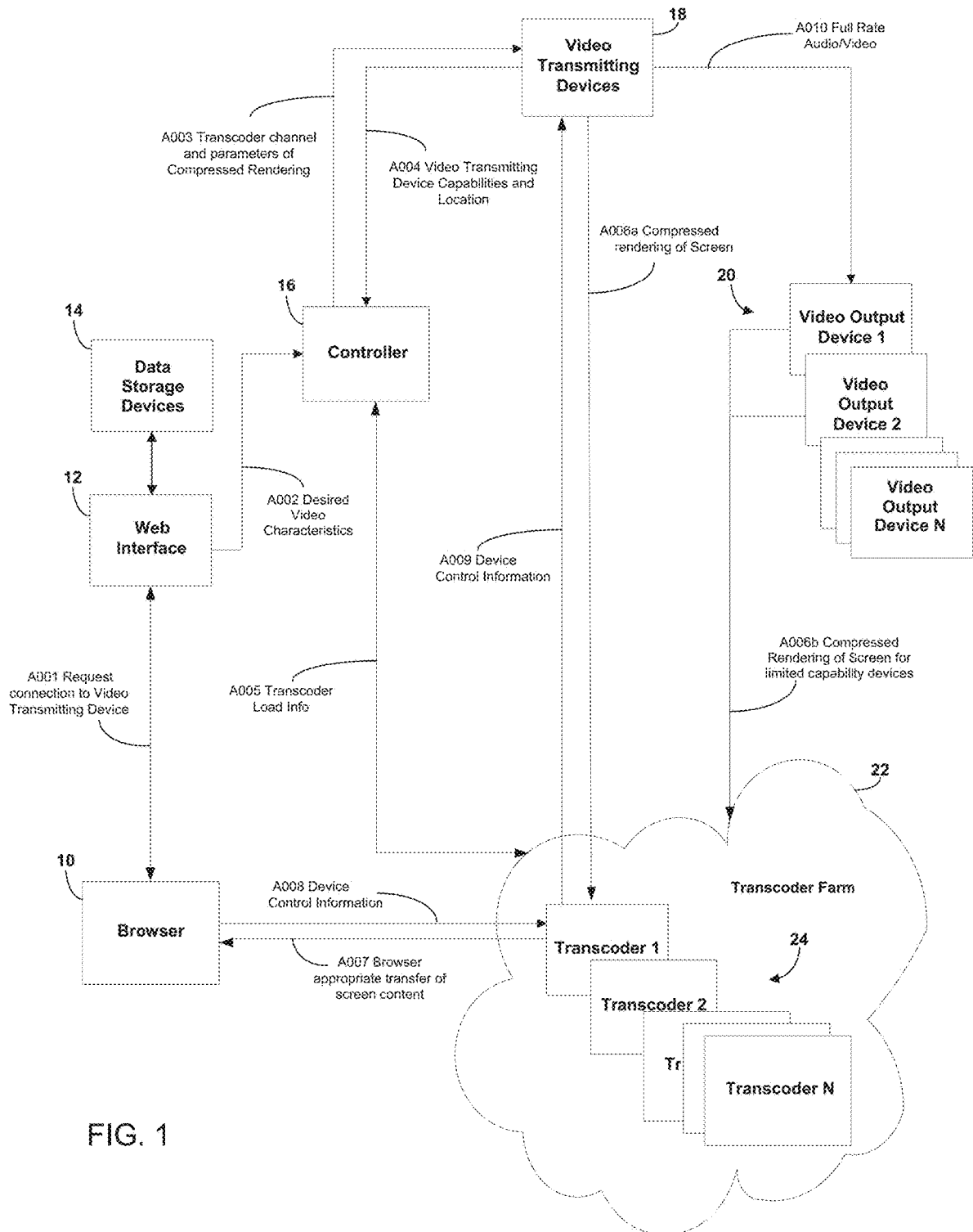
FIG. 1 is a schematic diagram of various components of a system for transmission of video data streams and a high-level description of data passed between components, according to an example embodiment.

FIG. 1 is a schematic diagram of various components of a system for transmission of video data streams and a high-level description of data passed between components according to some embodiments.

In particular, FIG. 1 depicts a Browser 10, a Web Interface 12, Data Storage Devices 14, Controller 16, Video Transmitting Devices 18, Video Output Devices 20, and a Transcoder Farm 22 including a plurality of Transcoders 24.

Browser 10 resides or runs on a computing device, and may be any modern web browser (e.g., Internet Explorer, Chrome, Firefox, Safari, or the like). As an example, Browser 10 may support HTML 5. Browser 10 may be a receiver side component for the video and audio data, but may also transmit data regarding desired video characteristics, control, parameters, and so on.

Web Interface 12 is a mechanism by which Browser 10 (and the computing device it resides or runs on) interacts with back-end Data Storage Devices 14 which contain information about Video Transmitting Devices 18, Video Output Devices 20 and their respective settings. Web Interface 12 may also reside or run on a computing device, as described below.

Data Storage Devices 14 (e.g., memory, and the like) could include a relational database (such as a SQL database), or other suitable data storage mechanisms. Data Storage Devices 14 are operable to store data records relating to video and audio data streams, control data, parameters, and the like. One or more of Data Storage Devices 14 may be cloud based, and may be accessible to computing devices through a cloud services interface. Cloud computing generally is the use of computing hardware and software resources that are delivered as a service over a network to computing devices. Data Storage Devices 14 may include any type of computer memory that is located either internally or externally such as, for example, RAM, read-only memory (ROM), CDROM, electro-optical memory, magneto-optical memory, EPROM, and EEPROM, FRAM or the like. In some embodiments, there may be one or more backup servers (not shown) that may duplicate some or all of the data stored on Data Storage Devices 14. The backup servers may be desirable for disaster recovery (e.g., to prevent undesired data loss in the event of an event such as a fire, flooding, or theft). In some embodiments, the backup servers may be directly connected but located at a different physical location.

Data Storage Devices 14 may be used to store data to provide video time-shifting or video replay, as described below.

Controller 16 is a matching/dispatching service which connects to both Video Transmitting Devices 18, Transcoder Farm 22, and in some applications, to Video Output Devices 20, and routes traffic between them. Controller 16 may be implemented as a computing device, as described below.

Each Video Transmitting Device 18 may be a transmitter (or camera/transmitter combination, such as a smartphone, tablet, laptop, or the like), which captures, encodes and sends a video and audio data stream to be broadcast (along with state information and video previews). Accordingly, Video Transmitting Device 18 is a transmitter side component for video and audio data, but may also receive data regarding desired video characteristics, control, parameters, and so on. Video Transmitting Device 18 may include hardware for generating video and audio data, a video and audio encoder, along with transmission and networking hardware. Video Transmitting Device 18 may be a dedicated purpose computing. Video Transmitting Device 18 may be implemented as a computing device, as described below. In some embodiments, Video Transmitting Device 18 may be a wireless mobile computing device, such as a smart phone, a super phone, a tablet and other mobile device with one or more built-in cameras, and may be capable of capturing, encoding and transmitting video and audio data. Video Transmitting Device 18 may transmit audio and video encoded data from a live source, for example a video camera, a high-definition wireless mobile device such as a mobile phone with digital camera capabilities, a tablet computer, etc., or from a stored source like a disk or other storage media. Video Transmitting Device 18 may refer to any sort of wireless mobile device being used to transmit data streams to a destination.

It is noted that the disclosure refers extensively to audio and video data, in part because audio and video data constitute an example where resources and computing capabilities may not be sufficient to provide adequate reliability based on a range of applications or user requirements. Embodiments described herein may be used to improve resource usages, computing efficiency, and other performance aspects for other applications, outside of transmission of audio data or video data, including for example the various other examples provided below that may not involve transmission or audio data or video data.

Each Transcoder 24 may be a computing device which receives encoded information from a Video Transmitting Device 18 and prepares it for delivery to Browser 10. Optionally, each Transcoder 24 may be paired with a particular Video Transmitting Device 18 and thereby be designated to receive encoded information from the particular Video Transmitting Device 18. Transcoder 24 may perform additional processing, such as in relation to a multipoint distribution scenario, for example. Transcoder 24 may take control information from Browser 10, and relay it to Video Transmitting Device 18 (via Controller 16) or Controller 16 may relay this information directly to Video Transmitting Device 18. Additionally, Controller 16 may serve to act as a static host to allow remote control when both the controllee and controller are behind a Network Address Translation (NAT), and perform the coding/proxying of the remote control data (in both directions) so that the controlling user can be using any recent Browser 10, with no native clients or plugins required.

In some embodiments, Transcoder 24 may send return video, e,g, video from a studio, to a Video Transmitting Device 18. In such embodiments, Transcoder 24 may transcode the video into a format displayable on that Video Transmitting Device 18.

Transcoder Farm 22 represents a collection of Transcoders 24. Transcoder Farm 22 could be implemented as a cloud based service, and managed by a third party and serving multiple Television Stations or other Broadcasters. Alternatively, Transcoder Farm 22 could be implemented using dedicated hardware located in a specific location (such as the central office of a broadcasting company or station, or at a temporary remote location for a special event) serving a single Television Station or Broadcaster. Transcoder Farm 22 could also be automatically scalable in a cloud environment, so as to provide for additional computing, memory or network resources in cases where a major event causes a surge in the amount of content available (e.g., UCG). In this scenario, the load on Transcoder Farm 22 as monitored by Controller 16, which may automatically scale up and down the computing capability of Transcoder Farm 22 as required.

Each Video Output Device 20 is a decoder which takes encoded full-rate, broadcast quality audio/video and prepares it for broadcast to the end location (e.g. a television studio, a website or a content distribution network (CDN) that provides website content to many users simultaneously). Video Output Device 20 may be a dedicated purpose computing device or it may be cloud computing resource that transmits data according to a Real Time Messaging Protocol (RTMP) or similar streaming protocol to a CDN. The streaming protocol may be a standard streaming protocol or a proprietary streaming protocol.

The components depicted in FIG. 1 may be interconnected by way of one or more networks, across a plurality of wireless transfer channels or links, and for each such channel or link there may be a receiver and transmitter side components, which may be different depending on the data between transmitted and received.

Figure 2:
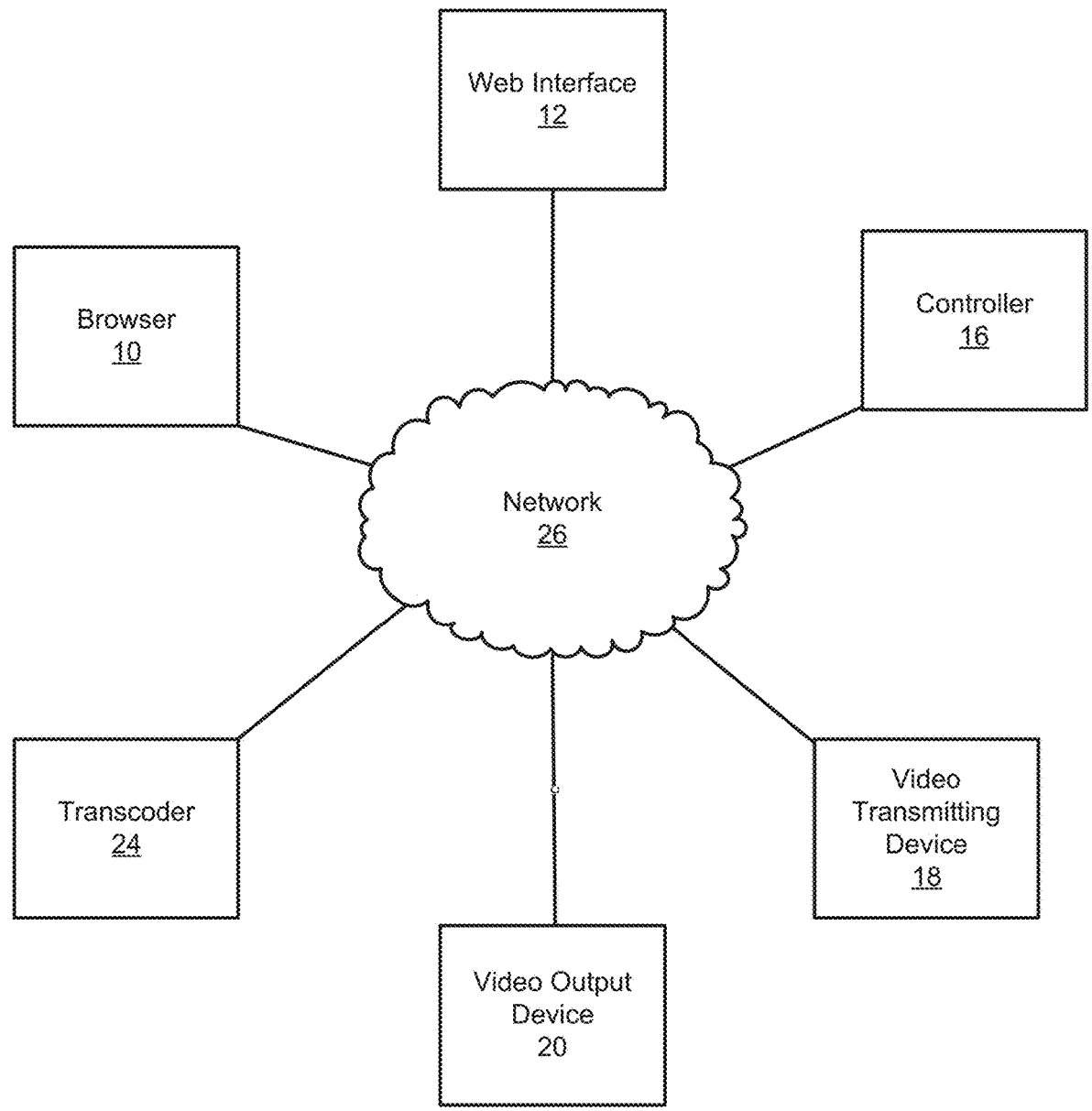
FIG. 2 is a network diagram illustrating a communication network interconnecting components of FIG. 1.

For example, FIG. 2 illustrates a Network 26 interconnecting Browser 10, Web Interface 12, Controller 16, Video Transmitting Device 18, Video Output Device 20, and Transcoder 24. Of course, Network 26 may also interconnect additional components, e.g., one or more additional Video Transmitting Devices 10, one or more additional Video Output Device 20, and/or one or more additional Transcoders 24 (e.g, as part of Transcoder Farm 22, or one or more Data Storage Devices 14). Some or all of these components may be distributed over a wide geographic area or even globally. This allows, for example, video to be transmitted from remote locations in the field.

Network 26 may be any network capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

Figure 3:
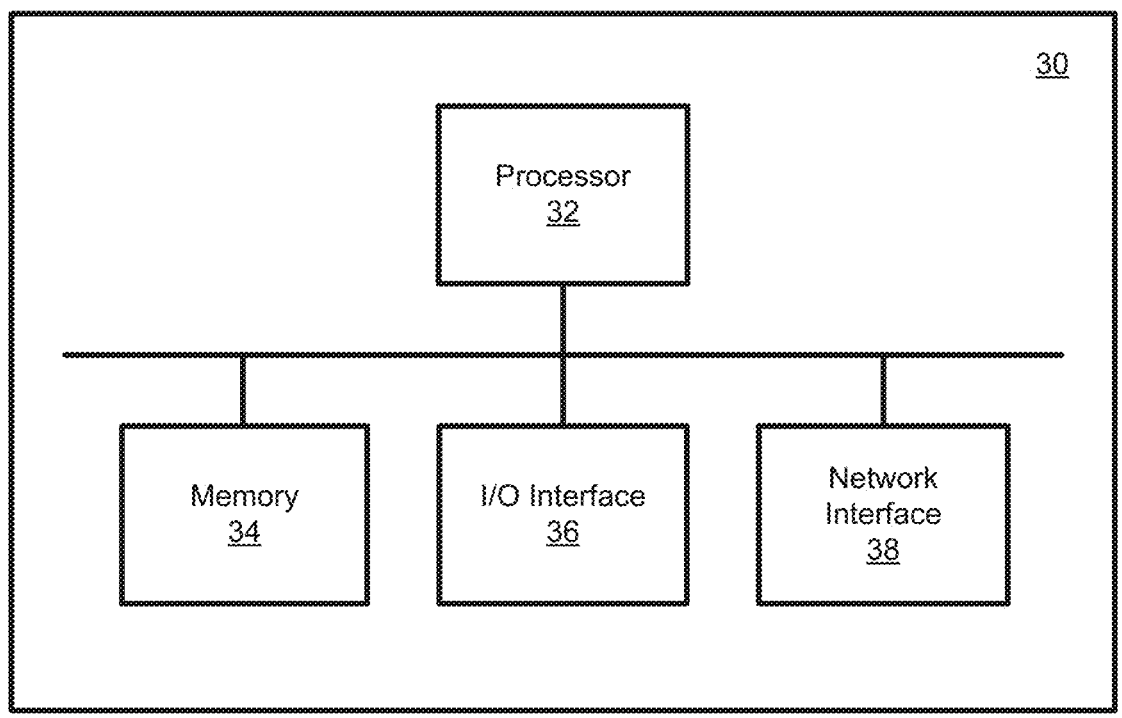
FIG. 3 is a high-level block diagram of a computer device adaptable to function as components of FIG. 1.

FIG. 3 is a schematic diagram of a computing device 30 that may be adapted to provide one or more of the components depicted in FIG. 1. Multiple computing devices 30 may be adapted to provide respective ones of the components depicted in FIG. 1. For example, a computing device 30 may be adapted to host Browser 10, another computing device 30 may be adapted to host Web Interface 12. Yet other computing devices 30 may be adapted to provide Controller 16, Video Transmitting Devices 18, Video Output Devices 20, and Transcoders 24.

So, in embodiments, each computing device 30 may be any network-enabled computing device, such as a personal computer, workstation, server, portable computer, mobile device, personal digital assistant, laptop, tablet, smart phone, WAP phone, an interactive television, video display terminals, gaming consoles, electronic reading device, and portable electronic devices or a combination of these.

As depicted in FIG. 3, computing device 30 may include at least one microprocessor 32, memory 34, at least one I/O interface 36, and at least one network interface 38.

Microprocessor 32 may be any type of processor, such as, for example, any type of general-purpose microprocessor or microcontroller (e.g., an Intel™ x86, PowerPC™, ARM™ processor, or the like), a digital signal processing (DSP) processor, an integrated circuit, a field programmable gate array (FPGA), or any combination thereof. Microprocessor 32 may also include special purpose logic for performing real-time audio/video encoding and decoding (such as Intel™ Quick Sync or the like).

Memory 34 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), or the like.

I/O interfaces 36 enable computing device 30 to interconnect with input and output devices. For example, when computing device 30 is adapted to provide video transmitting device, one or more I/O interfaces 36 may enable computing device 30 to interconnect with one or more cameras. I/O interface 36 may enable computing device 30 to interconnect with other input/output devices such as a keyboard, mouse, touch screen and microphone, display screen, speaker, or the like.

Network interfaces 38 enables computing device 30 to communicate with other components by connecting to one or more networks such as network 26. Computing device 30 may be operable to access network connections by way of network interfaces 38 singly or in unison.

An example process flow involving the components of FIG. 1 will be described with reference to the data links depicted in FIG. 1 and the flow chart blocks depicted in FIG. 4.

Browser 10 may request a connection to a Video Transmitting Device 18 (or multiple Video Transmitting Devices 18) through Web Interface 12 (link A001 of FIG. 1).

Figure 4:
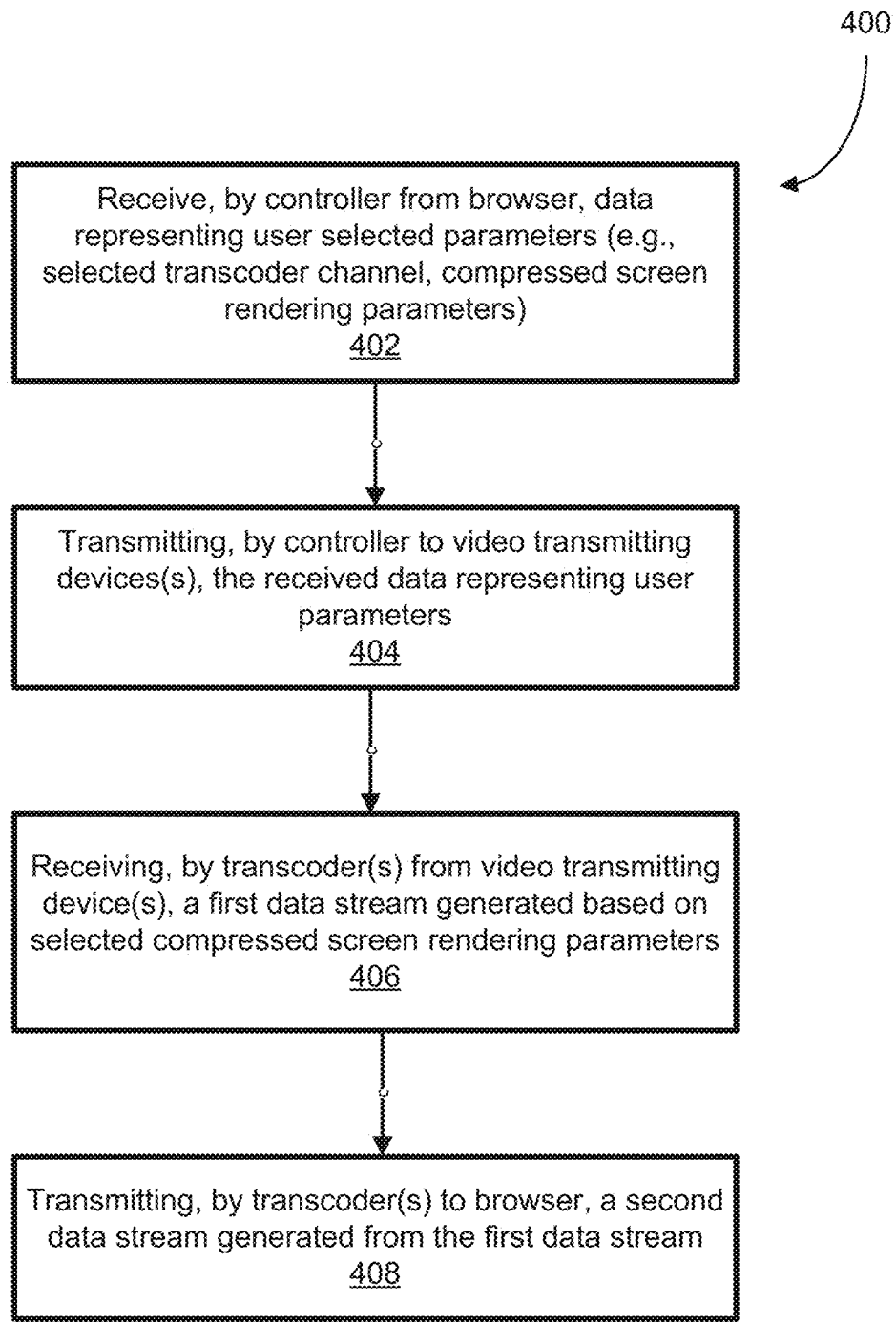
FIG. 4 is a flow chart depicting exemplary blocks performed by the system of FIG. 1, according to an example embodiment.

Web Interface 12 relays this information to Controller 16 along with the set of user selected parameters (link A002 of FIG. 1; block 402 of FIG. 4). The parameters may relate to encoding parameters for a compressed rendering of the preview screen and the Transcoder channel to which video and audio data should be directed. These parameters may include, but are not limited to resolution (e.g., 320×240 or 640×480), frame rate (e.g., 1 frame per second or 30 frames per second), bit rate for the requested stream (e.g., 40 kilobits per second or 512 kilobits per second), color depth (4, 8, 16 or 32 bits per pixel), transcoder availability, preview image versus entire video encoding device UI and cost. Selection of these parameters may not be mutually exclusive and that Controller 16, Browser 10 and/or Transcoder 24 may make calculations and apply predetermined rules to ensure that the result of provided parameter set results in a reasonable outcome.

Controller 16 then communicates with Video Transmitting Device 18 (link A003 of FIG. 1; block 404 of FIG. 4) indicating the parameters, such as for example, parameters of the compressed rendering of the preview screen (e.g. stream), and the Transcoder channel to which it should be directed. Controller 16 may also transmit information indicating which user has taken remote control of Video Transmitting Device 18 so that Video Transmitting Device 18 can display this information. Video Transmitting Device 18 may also indicate to the user through graphical or other means that it is under remote control.

Video Transmitting Device 18 responds to Controller 16 with its capabilities, location (e.g., GPS coordinates), and status (link A004 of FIG. 1). Video Transmitting Device 18 may also report network performance information (e.g., data rates, latency, lost packets, etc.) This information flow may be continuously occurring (e.g., in real time), so that Controller 16 has up-to-date information. Alternatively, Video Transmitting Device 18 can continually report status information (capabilities, location etc.) to Controller 16 at regular intervals via packet-based communication. Any such information received by Controller 16 may be relayed to Browser 10 for display to an operator. Conveniently, this allows the operator to monitor operating conditions of Video Transmitting Devices 18 in the field. Any such information may also be stored by Controller 16, e.g., in Data Storage Devices 14, for later retrieval and analysis.

Controller 16 monitors data regarding Transcoder Farm 22 (link A005 of FIG. 1) for computing, network and memory load information to determine which Transcoder 24 Video Transmitting Device 18 should send its data to. Transcoder Farm 22 may continuously provide this information to Controller 16. Alternatively, Transcoder Farm 22 can report computing, network and memory load information and network parameters (addresses etc.) to Controller 16 at regular intervals.

Video Transmitting Device 18 may transmit audio and video that may have originated from cameras or some other advanced capture method, or the information may have been pre-captured and saved to a storage media to be transferred at a later time. After preparing the audio and video data into buffers, Video Transmitting Device 18 may provide a steady and continuous flow of video and audio data to a receiver (e.g. Browser 10 or Video Output Device 20) as will be described herein. The system optionally provides the ability to modify the desired video quality at the source. Video quality can be dynamically adjusted (improved or degraded) in response to real-time feedback regarding network conditions that is obtained by Video Transmitting Device 18, from Controller 16, from Video Output Device 20 and/or from Network 26 both locally and remotely.

At Video Transmitting Device 18, the video source data may be prepared for transmission and moved into the video buffers, which may contain a storage component used to store data or video information. Many video buffers for example could be used and the data may be divided between the various buffers with each video buffer providing data to a separate network connection. Captured information can include, for example, normal, high or extremely high definition audio and video content. Preparation may include advanced compression (for example moving picture expert group (MPEG) compression), packetization and other processes designed to improve transmission. In some embodiments, video data from a single source, either live or stored, can be divided into multiple video streams using a technique like Multiple Descriptive Coding (MDC). Other techniques can also be used to break the video data stream into different packets for delivery over various links. The division of the data is intended to allow for wireless delivery of data in one or more video buffers over one or more wired or wireless network links, over one or more wired or wireless networks (e.g., Network 26 of FIG. 2). Each of the processes shown can be executed within one or more computer systems and the division of labor between computer systems may be based on processing unit utilization, network capacity or memory restrictions. Depending on conditions and processing unit availability, a complex video splitting method like MDC can be used or a packetization and splitting method could be substituted in its place, as disclosed for example in U.S. application Ser. No. 12/499,151, filed Jul. 8, 2009, the contents of which are incorporated by reference in their entirety). Within this encoding stage, the resolution, number of frames-per-second (FPS) and encoding quality is determined and the output enables dynamic adjustment of the quantity of information that is placed into the video buffers and subsequently transmitted.

Accordingly, Video Transmitting Device 18 generates a compressed rendering of the audio and video signal it receives (e.g. audio and video data stream) and sends the rendering to Transcoder 24 (link A006a of FIG. 1; block 406 of FIG. 4) over a wired or wireless network(s) (e.g., Network 26 of FIG. 2). Video Transmitting Device 18, if it has sufficient computing capability, may optionally encode the video that is rendered in compressed form to its Screen or preview window, including status, performance as user interface information, and send this compressed rendering to Transcoder 24 (the "screen rendering"). It may separately encode the incoming audio and video stream using parameters (e.g., resolution, frame rate and data rate) that are provided by Controller 16 or Browser 10 to provide a "preview stream". If the stream is directly encoded, the UI, status and performance information may be overlaid in the cloud by Transcoder 24.

Note that when Video Transmitting Device 18 has low computing capabilities, Video Transmitting Device 18 may transmit full rate audio/video to Video Output Device 20 or Transcoder Farm 22. Video Output Device 20 or Transcoder Farm 22 may decode and re-encode (i.e., transcode) this stream to the resolution, frame rate and bit rate that is requested for preview purposes in Browser 10. This may be based on the Full Rate Audio/Video being sent to Video Output Device 20 from Video Transmitting Device 18 for broadcast (link A010 of FIG. 1), thereby offloading the computational effort from the low-capability Video Transmitting Device 18. Video Output Device 20 may provide some of the video and audio processing described herein in relation to different components to offload computational requirements of those components. Video Output Device 20 may forward the screen rendering or preview stream to Transcoder 24 for further processing (link A006b of FIG. 1). Video Output Device 20 might also be used to perform the rendering/preview in cases where Video Transmitting Device 18 has high computing capabilities, but faces network or connection bandwidth constraints. In situations where a low computing capability Video Transmitting Device 18 is not transmitting full rate audio/video, it may be encode and transmit a low rate, compressed rending of the video and user interface (in the case where remote control is used).

Alternatively, Controller 16, under control of Browser 10 (and therefore a user operating Browser 10), may instruct a specific Video Transmitting Device 18 to switch from low rate audio/video (used for preview and/or remote control purposes or in a multi-viewer) to a full rate audio/video stream when the specific Video Transmitting Device 18 is selected for full rate audio/video output in a multi-viewer scenario (see FIG. 6) or when the User requests a full rate preview under remote control.

Transcoder 24 is operable to take the compressed screen rendering and re-encode it in a browser-friendly format (e.g., static JPEG images, supported compressed video formats or similar) which is sent to Browser 10 (link A007 of FIG. 1; block 408 of FIG. 4). The browser-friendly format may be described in the data provided by Browser 10 to Controller 16.

In accordance with some embodiments, Browser 10 is operable to communicate control information back to the specific Transcoder 24 (link A008 of FIG. 1) which is part of Transcoder Farm 22. The specific Transcoder 24 is operable to translate the control information and relay it to Video Transmitting Device 18 for processing (link A009 of FIG. 1). In other embodiments, Browser 10 is operable to communicate control information to Controller 16. Controller 16 is operable to relay the control information to the appropriate Transcoder 24 for translation and to Video Transmitting Device 18 for processing. The control information may include remote control information for controlling Video Transmitting Device 18, for example.

In some embodiments, Controller 16 may relay messages to Video Transmitting Devices 18, in the form of interruptible fold back (IFB) messages, chat messages, text messages, or the like. Such messages may be received by Controller 16 from, for example, a studio operator or a user operating Browser 10.

Figure 5:
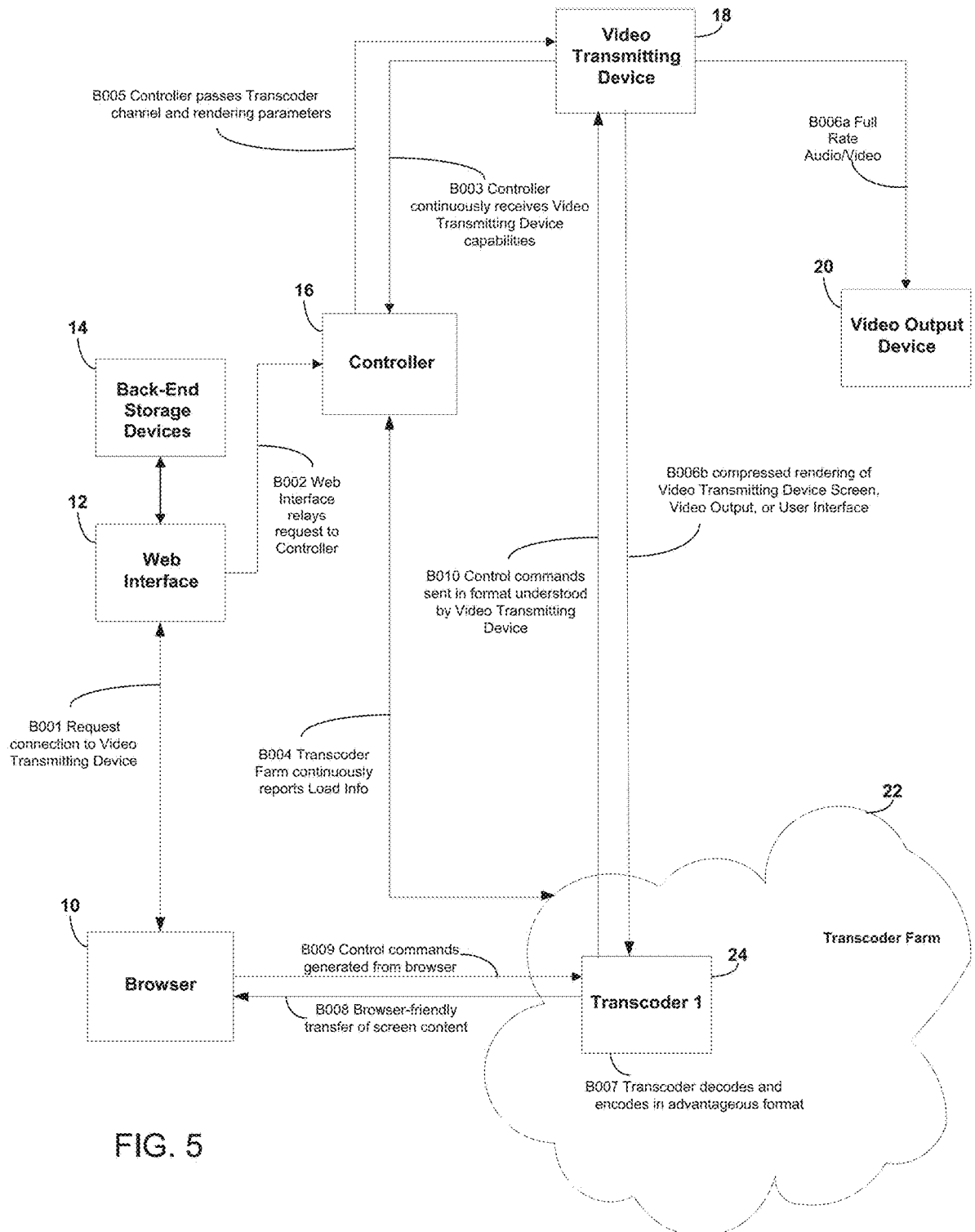
FIG. 5 is a schematic diagram of various components of a system for transmission of video data streams and a high-level description of data passed between components in the context of a remote control scenario wherein a user (e.g. content consumer) wishes to access the state of a remote video source and control its operation, according to an example embodiment.

FIG. 5 is a schematic diagram of various components of a system for transmission of video data streams and a high-level description of data passed between components in the context of a remote control scenario wherein a user wishes to access the state of a remote video source and control its operation according to some embodiments.

One scenario in which the system may be used is in remotely controlling a Video Transmitting Device 18, which is described hereinafter with reference to the data links depicted in FIG. 5.

In this scenario, a remote user requests a connection to a specific Video Transmitting Device 18 via Browser 10 by contacting Web Interface 12 (link B001 of FIG. 5).

Web Interface 12 then reports the request to Controller 16, including the parameters relating to compressed rendering of the preview screen (e.g. frame rate, resolution and target bitrate of the compressed rendering that will be viewed in Browser 10, desired video dimension of the preview video to be sent to Browser 10) (link B002 of FIG. 5). Selection of these parameters is not mutually exclusive and that Controller 16, Browser 10 and/or Transcoder 24 may make calculations and apply predetermine rules to provide ensure that the result of provided parameter set results in a reasonable outcome.

Controller 16 may receive information from Video Transmitting Device 18 regarding its capabilities (in terms of computational capability, memory availability, ability to encode multiple simultaneous video streams and available transmission bandwidth) (link B003 of FIG. 5).

Controller 16 is operable to receive load information (e.g. computation load, memory availability and network bandwidth available) from Transcoder Farm 22 to select the best available Transcoder 24 or to automatically provision additional Transcoders 24 as necessary (e.g. in embodiments in which Transcoder Farm 22 is automatically scalable). That selection may be related to both the load on the particular Transcoders 24 and the location of the particular Video Transmitting Device 18 relative to Transcoder Farm 24, which could itself be distributed geographically in the cloud so as to minimize latency between Video Transmitting Device 18 and Transcoder 24 or Video Transmitting Device 18 and Video Output Device 20 (link B004a of FIG. 5). Transcoder Farm 22 is operable to respond with the particular Transcoder 24 to be utilized (link B004b of FIG. 5), which in this illustrative example is Transcoder 1 (FIG. 5).

Controller 16 then provides the Transcoder channel to Video Transmitting Device 18 based on reports from Transcoder Farm 22, and the parameters of the desired compressed rendering based on the capabilities of Video Transmitting Device 18 (link B005 of FIG. 5), and the capabilities of Browser 10 (or of the bandwidth of the internet connection available to Browser 10 and the Internet). The data reported by Transcoder Farm 22 to Controller 16 may include, but are not limited to current computation load information, memory usage information, network bandwidth information along with available capacity for each of these parameters. Data may be reported periodically, when computational loads exceed a preset threshold or when Controller 16 requests this information.

Video Transmitting Device 18 is operable to generate a compressed rendering of the Video Transmitting Device Screen, Video Output, or User Interface which is then sent to the specified Transcoder 24 over a single or bonded connection. This compression (which will may involve a lower resolution, lower bitrate and frame rate) may enable efficient use of bandwidth (e.g. Video Transmitting Device 18 may be simultaneously transmitting full-rate video to Video Output Device 20 for broadcast), and may minimize latency (which may improve the responsiveness for the user controlling the device).

Video Transmitting Device 18 may send its state information and video preview in various ways. For example, Video Transmitting Device 18 may send a low quality complete representation which Transcoder 24 converts to an efficient Browser-friendly format displayable in Browser 10. As another example, Video Transmitting Device 18 may send a low quality video stream, and UI state information or UI vector graphics representation. Transcoder 24 dynamically renders a UI and overlays it on the video stream before or after rendering the browser format. Transcoder 24 may also introduce current connectivity statistics and or stream state to the render overlay. As a further example, Video Transmitting Device 18 may send a full rate stream to the Video Output Device 20 (link B006*a* of FIG. 5). Video Output Device 20 renders a lower bit rate version and sends that to Transcoder 24 for conversion (link B006*b* of FIG. 5). Again, Transcoder 24 may overlay connection statistics/status as necessary. This method may be more suitable for output verification. Video Transmitting Device 18 may also send a full rate stream to Transcoder 24 and Transcoder 24 may then decode and re-encode (i.e., transcode) the audio/video stream to the low rate, lower resolution browser friendly format that is required for rendering in Browser 10. The state information for Video Transmitting Device 18 may include, but is not limited to network connection status (bandwidth), overall stream health indicators, latency for each or a subset of the connections and/or information regarding the target encoder bitrates, status of UI buttons/controls, etc.

In the field, Video Transmitting Devices 18 are often bandwidth constrained (e.g. mobile devices using cell networks or slow DSL lines to transmit). By compressing the video preview from a Video Transmitting Device 18 to Transcoder 24, the solution described minimizes the bandwidth required for the multi-viewer and remote control functions to occur, allowing for more of the limited bandwidth to be used to provide the full rate video to Video Output Device 20. This reduced bandwidth may also have the advantage of reducing the cost of providing the remote control and multi-viewer service.

Once Video Transmitting Device 18 has sent its information, Transcoder 24 then decodes the compressed rendering from Video Transmitting Device 18 and re-encodes it in a browser-friendly format (B007 of FIG. 5).

Transcoder 24 sends that new screen rendering to Browser 10 (link B008 of FIG. 5). By re-encoding and transmitting in a browser-friendly format (e.g. static JPEG via WebSocket (HTML 5), supported compressed video formats or similar), the end user may use any modern browser without worrying about compatibility with Video Transmitting Device 18.

In some embodiments, the re-encoded stream sent by Transcoder 24 to Browser 10 may have a higher data rate than the stream received by Transcoder 24 from Video Transmitting Device 18. Such an increase in the data rate may result from re-encoding the screen rendering into a browser-friendly format displayable in Browser 10 without a browser plugin. In one embodiment, the data rate of the re-encoded stream may be 4-10 times higher than the data rate of the stream received from Video Transmitting Device 18.

Now seeing the screen rendering of Video Transmitting Device 18 in Browser 10, the user can send control commands to Video Transmitting Device 18 via Browser 10. These may include Mouse events, keyboard events, gestures, Start/Stop stream commands, commands to change the latency, input format or video resolution along with chat, text or return audio or video direction generated from Browser 10. Any type of settings or parameter change used by Video Transmitting Device 18 may also be sent as a control command.

In accordance with some embodiments, the control commands may be translated by Controller 16 or Transcoder 24 to match the capabilities of Video Transmitting Device 18 (link B010 of FIG. 5) and may be processed by Video Transmitting Device 18 or an operator of Video Transmitting Device 18, such as in the case of text, chat or audio instructions (e.g. to change positioning of the camera to obtain a different shot). In other example embodiments, such as the case where the camera or Video Transmitting Device 18 has integrated pan, tilt and zoom, the control commands may be processed by Controller 16 including text, chat or audio instructions and converted to equivalent commands that are processed, interpreted and automatically acted upon by Video Transmitting Device 18.

As this occurs, Video Transmitting Device 18 may still be sending screen renderings, which will reflect the changes requested by the user back to the user via Browser 10, allowing for further control commands to be sent based on the new state of Video Transmitting Device 18.

When a Video Transmitting Device 18 is under remote control, it is convenient to have a method of clearly indicating this state. For example, the display can be surrounded by a border with a specific colour. This is a non-limiting illustrative example, and other mechanisms may be used to indicate state.

It may also be convenient to show on Video Transmitting Device 18 who (user name or other user identification) has initiated a remote control session with that Video Transmitting Device 18.

When a Video Transmitting Device 18 is under remote control, it may be desirable to enable local lock-out of the user interface on that Video Transmitting Device 18 so that the user in the field is not attempting to adjust controls while they are being adjusted under remote control. This is an optional feature.

Access to remote control may be permitted via user access levels and credentials set by rules managed in Controller 16. Controller 16 is operable to present a UI via Browser 10 and this UI may allow for specific users to have "viewer only" privileges (i.e., they can view one or more remote control sessions that are in progress but they cannot initiate remote control sessions); "full control" privileges (i.e., they can initiate one or more remote control sessions that is in progress but they cannot initiate remote control sessions); or "super user" privileges (i.e., they can do everything that allows for "full control" and they can also stop other remote control sessions and perform other administrative tasks).

Although only one Browser 10 is shown in FIG. 5, it is possible to have multiple remote control sessions (with video preview and control of a Video Transmitting Device 18) simultaneously.

Figure 6:
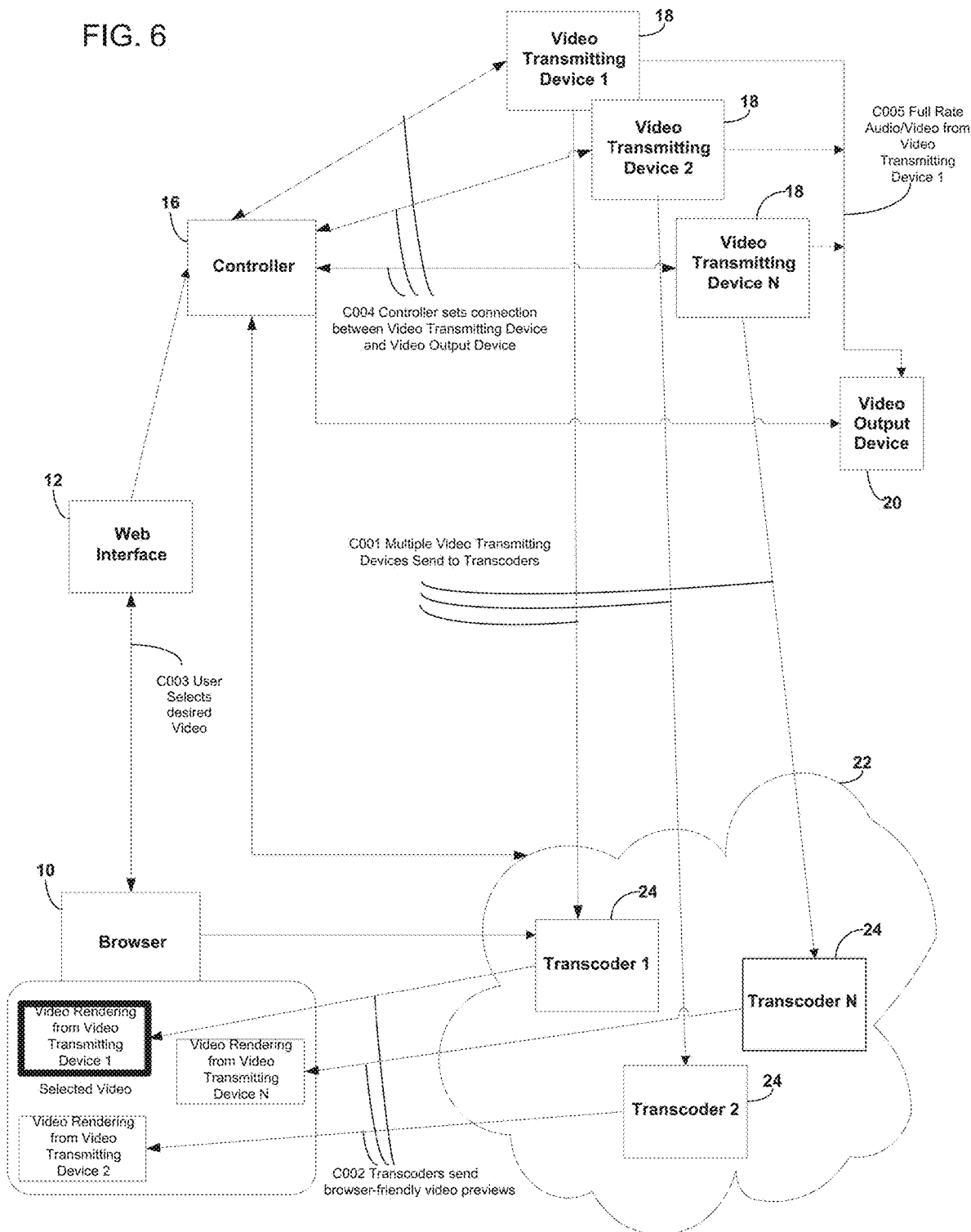
FIG. 6 is a schematic diagram of various components of a system for transmission of video data streams and a high-level description of data passed between components in the context of a multi-viewer scenario wherein a user (e.g. content consumer) wishes to visualize the output of multiple video sources, according to an example embodiment.

FIG. 6 is a schematic diagram of various components of a system for transmission of video data streams and a high-level description of data passed between components in the context of a multi-viewer scenario wherein a user wishes to visualize the output of multiple video sources according to some embodiments.

Another application suited to this system is that of a multi-viewer, where the user (content consumer or content manager) wishes to preview numerous live video inputs simultaneously in a single location, so as to choose which video input (or inputs) to broadcast (provided to content consumers), which is described hereinafter with reference to the data links depicted in FIG. 6.

For this scenario, Video Transmitting Devices 18 may have already been paired with Transcoders 24 as discussed herein.

Multiple Video Transmitting Devices 18 are operable to send compressed video previews to multiple Transcoders 24, generally via bonded connections or adaptively bonded connections (link C001 of FIG. 6).

Again, while not specified in FIG. 6, it should be noted that a low computing capability Video Transmitting Device 18 may have its preview compressed by a Video Output Device 20 that they may be attached to (as per link A006b of FIG. 1). Alternatively, a low computing capability Video Transmitting Device 18 may send a low rate audio/video stream to Transcoder 24 and when selected for output to Video Output Device 20, switch (as dictated by Controller 16) to a high rate audio/video stream. As outlined above, Video Transmitting Devices 18 with sufficient computing capability can send simultaneous low rate and high rate audio/video streams. The low rate stream may be used for preview purposes and the high rate stream may be for fast switching to Video Output Device 20, should the specific Video Transmitting Device 18 be selected for output.

In some embodiments, Video Transmitting Devices 18 may switch between sending low rate and high rate audio/video streams on demand, e.g., in response to a request from Controller 16. Such requests may be made automatically, for example, in response to changing network conditions, as monitored at Controller 16. Such requests may also be made manually, e.g., by an operator of Browser 10, which are relayed by Controller 16 to Video Output Device 24.

Transcoders 24 are operable to send video previews from their respective Video Transmitting Devices 18 in a browser-friendly format (link C002 of FIG. 6).

In some embodiments, Transcoders 24 may send video previews to Browser 10 in a uniform format (e.g., same resolution, same framerate, etc). So, when Transcoders 24 receives video previews from their respective Video Transmitting Devices 18 in disparate formats, Transcoders 24 may apply corresponding disparate transcoding operations to transcode the video previews into a uniform format.

The user then selects (via Browser 10) the video feed desired to be sent to Video Output Device (link C003 of FIG. 6), e.g., the video feed from Video Transmitting Device 1 as depicted.

In some embodiments, an operator in a control room, operating Browser 10, may request an expanded view of a video preview from a particular Video Transmitting Device 18, e.g., from amongst several video previews from several Video Transmitting Devices 18. In response to a request for such an expanded view, new pre-defined parameters for a compressed rendering of the preview screen are sent to Controller 16, for relay to the particular Video Transmitting Device 18. Typically, the new parameters reflect a modest increase in frame rate, bitrate or resolution of the video preview. So, an expanded view may be used, for example, by the operator to more closely inspect and thus better assess the quality of a shot before selecting a stream for broadcasting. The operator may of course toggle off the expanded view when it is no longer required, causing the lower parameters for the compressed rendering of the preview screen to be used once again.

Controller 16 then routes connection between selected Video Transmitting Device 18 and Video Output Device 20 (link C004 of FIG. 6) based on input from Browser 10.

Full Rate Audio/Video (full bitrate, full frame rate, full resolution) may then be sent to Video Output Device 20 by the selected Video Transmitting Device 18 (FIG. 3-005).

While FIG. 6 depicts a single Video Output Device 20 for clarity, the system is not limited to a single Video Output Device 20, so each Video Transmitting Device 18 may be sending data to a different Video Output Device 20 as per the routing instructions supplied by Controller 16.

For clarity it should be noted that when a full rate audio/video connection is selected, it may be routed directly from a selected Video Transmitting Device 18 to Video Output Device 20 because this provides the lowest latency and fastest switching of the selected video stream.

Figure 7A:
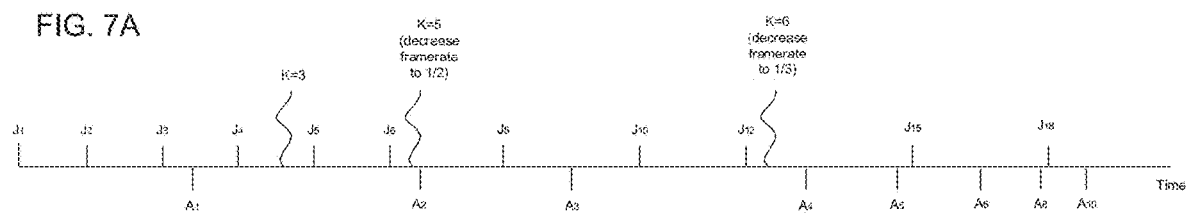
FIG. 7A and 7B illustrate timeline diagrams showing management of framerate based on feedback, according to an example embodiment.
Figure 7B:
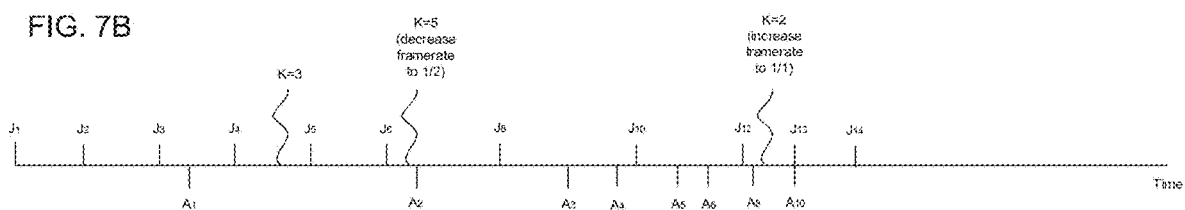

FIG. 7A and FIG. 7B illustrate timeline diagrams showing the management of framerates based on feedback. In particular, as detailed below, frame-rates may be dynamically and automatically adjusted based on feedback. Such management of framerates may be performed, for example, at Transcoder 24 to manage the frame-rate for the browser-friendly video previews sent to Browser 10. However, management of framerates as disclosed herein may also be performed at any other components of the systems described herein that transmit video frames.

FIG. 7A and FIG. 7B show a flow of preview frames in a video preview according to an example embodiment, where J is a video preview frame that has been sent (e.g., a JPEG file) and A is an acknowledgement that the frame has been received. K is the difference between the number of video preview frames sent and the number of acknowledgements that those frames have been received (i.e., K=#J−#A). In an embodiment, K may be calculated each time a preview frame is generated, thus varying the calculation (polling) interval according to the framerate. In another embodiment, the calculation of K may occur at a constant interval.

With reference to FIG. 7A, in some embodiment, when the number of frames being sent relative to the acknowledgements being returned (K) grows beyond a pre-defined value (X), i.e., when K>X, the rate at which preview frames (J) are sent, i.e., the transmission framerate, is reduced. This causes some preview frames captured in the field to be skipped. The transmission framerate may be increased once the number of acknowledgements (#A) catches up to the number of frames (#J).

In an embodiment, the decrease in transmission framerate is handled as an integer decimation (1, ½, ⅓, ¼, etc.) of the initial transmission framerate. This allows "stuttering" in the video preview feed to be avoided. For example, if the initial video preview transmission framerate is 30 frames per second, the first reduction would be to 15 frames per second, then to 10 frames per second, then 7.5 frames per second, then 6 frames, and so on.

With reference to FIG. 7B, in some embodiments, when the number of frames being sent relative to the acknowledgements being returned (K) decreases beyond a pre-defined threshold value (X), i.e., when K<X, the rate at which preview frames (J) are sent is is increased towards a target framerate. In an embodiment, this transmission framerate may be increased according to a variable interval which takes into account any subsequent decimations of the framerate. For example, an initial interval (e.g. 10 seconds) may be doubled (e.g. to 20 seconds) if the transmission framerate needs to be reduced again after a previous increase in the transmission framerate. In an embodiment, similar to decreasing the transmission framerate, increasing the transmission framerate may include applying a reversed integer decimation. So, for example, if the current transmission framerate is at ¼ of the target rate, it is increased to ⅓ of the rate, then to ½, and so on.

X may be a specific number of frames, or may be a function of a target number of frames based on a variety of factors, including, e.g., factors specific to the transmission mechanism or the desired latency. In an embodiment, X may be expressed as a function of the exponential moving average (EMA) of K, e.g., X=1.25*EMA(K), where the smoothing value of the EMA of K is set based on information about the nature of the network connection.

In some embodiments, a "time-shifting" effect may be created by sending the video preview at a very low latency (e.g. 1 second) and sending the full rate video at a higher latency (e.g. 8 seconds). A "time-shifting" effect may also be created by recording video on a Video Transmitting Device 18 for later playback (e.g., at the time that the operator selects the feed from that Video Transmitting Device 18).

So, an operator may use the low rate video preview to scan available video feeds and then select a desired full rate feed, and the "time-shifting" effect ensures that what the operator sees on the video preview will be transmitted to the Video Output Device 20. In contrast, when there is no "time-shifting" effect, the operator will only be able to select the audio/video from that particular Video Transmitting Device from the point of selection forward.

The "time-shifting" effect is further described with reference to an example scenario. In this scenario, an operator views a video preview from a Video Transmitting Device 18 with one second latency, which previews a full rate video feed with an 8 second latency from the Video Transmitting Device 18, and there is an initial five second delay between the time the operator selects the preview for transmission to a Video Output Device 20 (at time t=0 s), and the time the first frames from the video transmitter are sent to the video output device (at time t=5 s).

In the absence of the "time-shifting" effect, the first frame from the Video Transmitting Device 18 would arrive at the Video Output Device 20 at t=13 s (initial 5 second set-up delay plus 8 second latency), and would start with the frames captured at t=5 s. In contrast, in the presence of the "time-shifting" effect, while the first frame still arrives at the Video Output Device 20 at t=13 s, the first frames correspond to the frames captured at t=−1 s, i.e., the time the operator selects the preview for transmission (t=0 s), minus the 1 second latency.

As will be appreciated, the duration of the "time-shifting" may be user controlled and set to a desired value (e.g., start full rate video 3 seconds before the moment the preview video is selected by the operator) to allow the operator to fully preview a scene and then, deciding that it was of interest, select it for transmission by full rate video.

As noted, "time-shifting" may be provided by recording video data at Video Transmitting Device 18, however, the video data could also be recorded elsewhere to achieve the same effect. For example, in another embodiment, video data for "time-shifting" may be recorded at Data Storage Devices 14 or in the cloud. In a particular embodiment, video data may be recorded in a circular buffer, and pointers may be used to locate the position in the buffer to save data to, and the position in the buffer to read data from. The size of this buffer may be user definable, and may be adjusted dynamically during operation.

Video data may also be recorded at Data Storage Devices 14 or in the cloud for later retransmission and playback. Video data may be recorded in response to a user request (on demand), e.g., from an operator of Video Transmitting Device 18 or an operator of Browser 10. Video data may also be recorded according to a schedule, or in response to other user-defined conditions being met (e.g., available bandwidth exceeds a pre-defined threshold).

In a scenario where UGC is involved or when a Video Transmitting Device 18 is owned and operated by a user (content provider) who desires compensation for the contribution of their full rate audio/video content, the multi-viewer system is operable to support viewing of low rate audio/video streams without compensation to the content provider, in some example embodiments. However, when a full rate audio/video stream is selected (switched to Video Output Device 20) and Controller 16 indicates that this stream is a "pay" stream, the broadcaster (or other content consumer) may compensate the content provider on a per use or for the duration of stream use, for example. Other compensation schemes may also be used.

To provide this feature, content consumers may agree in advance or at the time of full rate audio/video stream selection to the compensation that will be provided to content providers. Controller 16 is operable to monitor the full rate audio/video stream usage and compute the monetary or other compensation that is due from the content user to the content provider. The operator of the multi-viewer system may also receive compensation for the use of the system.

Content consumers and managers may want to know that the content they are receiving is from a trusted source and a number of elements of the proposed system help to ensure that the content can be trusted. Authentication may be achieved in a variety of ways.

For example, all devices may incorporate a unique per device license. This license may be encrypted and "locked" to a device via a unique hardware signature (or similar) that is authenticated by Controller 16. This ensures that any device sending a broadcast is known and authenticated by Controller 16.

As another example, all users of the system may have unique credentials (user identification and password) that may be sent to Controller 16 via the Device Capabilities and Location link (link A004 of FIG. 1) so that the user sending the transmission to the system is also known and authenticated.

As a further example, all devices with geo-location capability (global positioning system, cellular tower triangulation or similar) may send their geo-location information to Controller 16 when this information is available. This may allow for authentication and tracking of the device location.

As another example, Controller 16 may incorporate a content provider rating system that allows content consumers and content managers to rate the quality and performance of the content that is provided by each content provider. Ratings for content providers can be viewed by content consumers if they have sufficient authorization on Controller 16. This rating system may allow for disputes to be addressed and resolved and ensures that high performing content providers are made known to and/or preferentially selected by content consumers or content managers.

As a further example, Controller 16 may incorporate an audio/video analysis subsystem that may analyze the audio and/or the video being received to ensure that it aligns with the expected content. For example, still video frames may be matched against a known database of images (e.g., Google street view) to ensure that the content location is as a reported. The audio signal may also be analyzed for language content (e.g., German versus English or keyword analysis in a target language) or for audio signatures (e.g., sirens, the sound of an explosion or live music) to ensure that the content is what is expected.

As an extension of the scenarios and systems described with reference to FIG. 5 and FIG. 6, a user may view the screens of multiple Video Transmitting Devices 18 (as per multi-viewer example) and then based on what they observe, select one or more of those devices to control remotely to adjust the settings of the specific Video Transmitting Device 18 or otherwise modify the characteristics of the video shot. The combination of these concepts provides a mechanism for a control room to manage both inputs and outputs from a single browser window within a single system.

FIG. 8 shows a schematic diagram of various components of a system for transmission of video data streams and a high-level description of data passed between components in the context multi-viewer and remote control functions to create a multipoint video distribution system in the cloud according to some embodiments.

It may also be desirable for multiple content consumers to receive the same full rate audio/video stream simultaneously (sometimes referred to as a "pool feed"). This can be advantageously combined with the architecture described above for multipoint distribution and remote control.

As an illustrative example scenario, there may be three Broadcasters A, B, and C. Each broadcaster may have one or more transmitters, shown as single Video Transmitting Devices 20, labeled as Video Transmitting Devices A, B, or C respectively for clarity.

Each of these Broadcasters may have a multi-viewer (as described with reference to FIG. 6) through which they are able to subscribe to each other's audio/video streams. This visibility may be approved either through a subscription agreement, or through a third party providing a video marketplace of available feeds, and would be managed by subscription rules in Controller 16. In this example scenario, one Broadcaster (e.g., Broadcaster C) may play the role of the content provider and the other plays the role of the contact consumer.

When content is provided, both reduced rate and full rate audio/video streams may be sent from Video Transmitting Devices 20 to Transcoding Farm 22. In Transcoding Farm 22, the low rate audio/video streams are provided as previews (see description for FIG. 6). Visibility of low rate audio/video preview streams may be managed using subscription rules in Controller 16. If a Broadcaster is authorized to view a low rate audio/video stream, they may be able to select and view it in their multi-viewer. Streams may be organized on different tabs in Browser 10 (for different categories, types or sources) so they can be selected and then appear in the multi-viewer tab (or window) of the Browser.

Device, user, location and audio/video authentication (as outlined above) may ensure that the content provided is from a trusted source.

When a low rate audio/video stream is selected, the content provider may be notified and the payment terms that form part of the subscription agreement (and that are managed as outlined in FIG. 6) are enabled. The selection of a stream may cause Transcoder 24 to enable a high rate audio/video stream from Transcoder Farm 22 to the particular Video Output Device 20 at the content consumer's location.

To ensure consistent performance and controlled latency, each high rate audio/video stream that is delivered may be managed by a separate Transcoder in the Transcoder Farm. If no changes are required to the video format, resolution or other audio/video characteristics similar the Transcoder may simply manage the buffering of the high rate audio/video stream to ensure that the latency to a specific end-point is controlled.

Through user managed subscription rules on Controller 16, this scheme can be readily extended to the scenario where the content providers are users providing UGC.

In an embodiment, one or more Transcoders 24 in Transcoder Farm 22 may each function as a "proxy" in the cloud that interconnects a Video Input Device 24 with a particular stream destination, e.g., a Video Output Device 24 or any other consumer of an audio/video stream. Transcoder Coder Farm 22 may include a dispatcher that dynamically assigns Transcoders 24 functioning as proxies to particular Video Input Devices 24 and particular stream destinations. This assignment may be based on factors including transcoding requirements, and availability of cloud resources. Transcoder 24 may be a transparent proxy, such that its operation and assignment are transparent to Video Output Devices 24 and stream destinations. Resource levels in Transcoder Farm 22 may also be monitored and controlled, e.g., by Controller 16, and the number of Transcoders 24 provided in the cloud may be adjusted dynamically. Conveniently, this provides scalability to Transcoder Farm 22, and facilitates delivery of streams to a large number of stream destinations.

A set of Transcoders 24 functioning as proxies may be used to provide multipoint distribution as disclosed herein, e.g., with delivery of streams to a multiple stream destinations.

In one example configuration of multipoint distribution, Transcoders 24 may operate in concert to deliver video streams at a guaranteed fixed latency to each stream destination. For each stream destination, a Transcoder 24 relays a video stream from a Video Transmitting Device 18 to that stream destination, and performs any transcoding required for that stream destination. Transcoding requirements for a Transcoder 24 may depend on the display capabilities of the stream destination or on characteristics of the network interconnecting the Transcoder 24 with the stream destination. Transcoder 24 may also relay any return communication from the stream destination to the Video Transmitting Device 18.

In another example configuration of multiple distribution, at least one of the stream destinations is designated as a primary destination, while remaining stream destinations are designated as secondary destinations. Transcoders 24 operate in concert to deliver video streams at a guaranteed fixed latency to the primary destination(s). Meanwhile, delivery of video streams to secondary destinations is performed without a guaranteed fixed latency. For example, delivery of video streams to secondary destinations may be performed on best efforts basis, or with adaptive latency. Transcoder 24 may transcode streams as required by each destination. In some cases, streaming to secondary destinations may not be in real time. Rather, video data may be delivered to a secondary destination to be buffered or otherwise stored for subsequent playback.

In some cases, a re-encoded stream may be shared amongst multiple Transcoders 24, such that the same re-encoded stream is sent to multiple stream destinations having the same or similar transcoding requirements. As will be appreciated, this reduces computational load on Transcoder Farm 22 as some repetition of transcoding may be avoided.

Accordingly, embodiments described herein may relate to content generation, live transmission to either hosted or private servers with management and control by controller components.

Referring now to FIG. 9, there is shown a schematic diagram of a System 100 for transmitting data streams according to some embodiments. As depicted, System 100 may include Video Transmitting Devices 18, a Controller 116, a Browser 10, Transcoders 24, and Video Output Devices 20 coupled via a network (e.g. the Internet or Network 26 of FIG. 2). These components are described in detail herein. Video Transmitting Devices 18 (via Transcoders 24, or directly) may transmit and metadata to Controller 116 and receive instructions, notifications, and routing information from Controller 116. These are non-limiting example data exchanges for illustrative purposes.

Controller 116 may include a Monitoring and Control Component 118, a Command and Control Portal 120, and an Access Rights Manager 122. Controller 116 may transmit and receive monitoring and control information to and from Browser 10. Controller 116 is otherwise substantially similar to Controller 16.

Video Transmitting Devices 18 may transmit content to Video Output Devices 20 and Browser 10 via Transcoders 24. The Video Output Devices may include hosted servers and private servers specific to content consumers. The servers may provide the content to different content consumers via CDN, SDI, Ethernet, SAT DVB-S2, etc. These are non-limiting examples for illustrative purposes.

In accordance with some embodiments, the systems and methods may enable real-time monetization or compensation for live video and audio data streams, for both amateur and professional videographers.

The proliferation of cameras and recording/broadcasting software/solutions is leading to a situation where hundreds of cameras may be present at an event and recording. Of those cameras only one or two may be newsworthy (due to clarity of the image, framing, content). Multiply that by the number of events that occur even in a single city on any given day, and the number of streams that must be managed is astronomical. In accordance with some embodiments, the systems and methods may provide multi-viewer and selection for broadcast, along with remote control.

Unknown reputations and random content make it difficult for a news director to commit to live video from amateur videographers. By creating a marketplace where content creators can become known for their quality, and, more importantly, be associated with the videos they produce, it becomes possible to provide some level of assurance of video quality. In accordance with some embodiments, the systems and methods may provide authentication of content providers.

There are multiple sources of information that can be used to describe a video stream in order to locate desired video content. Preference may be given to those forms of information that are collected automatically, without additional requirements from the camera operator/subscriber. Algorithm data and cryptographic signatures may be used to validate and/or verify a video stream. Based on the generated information, and additional data provided by the operator so that a video stream becomes searchable by news directors, and can be linked to relevant stories. Built-in GPS devices may record real time and physical location of the camera (e.g. Video Transmitting Device) at the time of stream capture. Capabilities in some cameras also allow the software to calculate the direction the camera is pointing. Location (geo location obtained via GPS, cellular tower triangulation or other means) searching can be used to locate relevant content.

Content Tags may be used to locate relevant content. The content tags may be generated via speech to text (e.g. voice recognition software either locally or server based processes received vocals and parses them for content/tags), ambient noise to text (e.g. software parses the received audio stream and translates sounds as text). In combination with the voice recognition, the resulting descriptive text could be used to identify the track, route based on keywords, or even supplement the closed captioning system. Content tags may be generated by text entry to describe the video where the operator may supply content tags. Content tags may be generated via image recognition to video description to identify content of video frames and convert to text descriptions.

The video and audio data stream may be linked with an identifier of the video source. The device, account the data is submitted under, the name of the camera operator, or a combination thereof may be encoded into the video stream as a watermark (or invisibly through steganography). Over time, an account/content generator may gain prestige either generally through a global ranking (public 95% content approval rating) and individually (white list, black list, internal/private station ranking).

There may be infinite number of possible video streams to select from, and these identification mechanisms may be used to identify relevant content. There may be a limited number of outputs in the station. A station may select appropriate content based on time, location, content tags, source, trustworthiness, etc. A search mechanism may allow a news director to narrow down the content to a manageable list using the above parameters on a weighted scale. There may be social network integration to track trends on social networks to identify current news worthy/trending topics and, based on that information, build a list of ranked available content. As topics trend higher, matching video may follow through the UI. There may be a mechanism to reward amateur providers (free airtime, tickets/prizes, cash, etc.) and pay freelancing professionals (cash).

Using a downloadable application, a user can connect to System 100, either as a freelancer or as an invited station guest. Freelancers may have their own account, set their own prices, and own/direct their content to the highest bidder. Guest streams may only be accessible by the hosting station only, and may be, in effect, a downloadable temporary license. The news director selects content for internal viewing, and may make video more publically available, either within the station group, or to the world at large or some subset in between. The news director may also responsible for assigning a trust level to guest content. A guest device may be blacklisted by a station, preventing that guest/device from acquiring another license and submitting video to that station until the issue is cleared. Guest streams may be limited by time, geo-location, or other parameters set by the news director. System 100 may provide stations with a branded application for Video Transmitting Devices 18, identifying that application as belonging to a given station (to reduce confusion if a user happens to be a guest of more than one station). It may be up to the station/news director to determine how guests are compensated. Given the expense to upload video, there may be some requirement(s) to manage bandwidth. A guest may start uploading or sending live in low bit-rate initially, and if selected for broadcast by the news director, transition the stream to full-rate (and begin to compensate appropriately). Station directors may submit instructions to their guests, requesting them to move, cover a different target or other feedback via remote controls (as described above).

Command and Control Portal 120 which may be part of Controller 116 and can be accessed via a web browser (e.g., Browser 10) may provide visual feedback on guest groupings (at an event), including where available, the current recording direction. In some circumstances, it may be desirable to support a sort of reservation/availability solution, where instead of a guest immediately recording video and submitting it live, they may instead indicate their location and willingness to provide video. If permission to record is granted, the session may be enabled. This may also tie in directly with the ability to compensate or reward guests for valuable video.

Joining a stream may imply that the news director has agreed to the terms and/or conditions set by the freelancer. The news director is free to negotiate further terms (exclusivity for instance) once they join the stream. Once a station director has joined a stream (guest or freelance), they may be able to send (text) data to the generator requesting changes and/or providing feedback (turn the microphone up, etc.) as described herein.

Money to operate the service may be generated by taking a portion of the transaction fees paid from the news directors to the freelancers and/or a direct payment from the studio(s) to manage/provide licences to their guest subscribers.

System 100 may maintain a global ranking system based on feedback from stations and consumers of content regarding: stream quality (both in terms of content, and broadcast readiness), appropriate labelling (does the content provided match what the videographer's description), professionalism (verified credentials, etc.), and so on. Integration with social networks (Twitter, Facebook, Google+, etc.) may allow the marketplace to provide trending information relevant to current available/active streams.

Live streams may also be recorded for later access/consumption by interested parties. Content creators may be responsible for managing their archive. The service may provide a limited quantity of free storage space. The service may also provide storage space for a fee (subscription or one time).

Content creators may be free to license their streams to as many or as few as they desire.

The marketplace may support a wide variety of content licences. Streams may be marked as freely available, limited (such a creative commons license - available with restrictions on use), or restricted (requiring compensation or an agreement for access).

Content, once received by the system servers may be delivered to the studio systems by a variety of means: SDI (e.g. a standard direct BNC connection into the station ingest directly from the server), CDN (content delivery network(s) wherein one or more organizations may be geared to providing high volume data to subscribers over the Internet), Ethernet TS (also known as Video over IP, a MPEG-2 transport stream encapsulated for delivery over an IP based network, where video stream data packets are delivered directly to the studio's systems, DVB-S2 (Digital Video Broadcasting Satellite Second Generation, making use of a satellite hop to transport an MPEG stream), and the like. The plurality of network connections of System 100 may include one or more or cellular, satellite, microwave, and wired Ethernet connections.

Throughout the foregoing discussion, numerous references are made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable media storing the instructions that cause a processor to execute the disclosed steps. One should appreciate that the embodiments described herein may provide various technical effects such as controlling video transmitting devices and quality of content transmitted thereby, selecting content and video transmitting devices from a large amount, scaling video transmission and processing, efficiently using and managing network and computing resources, authenticating of content and devices, management of compensation for content, efficiently encoding and transmitting video, and other example technical effects as described herein.

The foregoing discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example, and without limitation, the various programmable computers may be a server, network appliance, set-top box, embedded device, computer expansion module, personal computer, laptop, personal data assistant, cellular telephone, smartphone device, UMPC tablets and wireless hypermedia device or any other computing device capable of being configured to carry out the methods described herein.

Program code is applied to input data to perform the functions described herein and to generate output information. The output information is applied to one or more output devices, in known fashion. In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and combination thereof.

Each program may be implemented in a high level procedural or object oriented programming or scripting language, or both, to communicate with a computer system. However, alternatively the programs may be implemented in assembly or machine language, if desired. The language may be a compiled or interpreted language. Each such computer program may be stored on a storage media or a device (e.g., ROM, magnetic disk, optical disc), readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the systems and methods of the described embodiments are capable of being distributed in a computer program product including a physical, non-transitory computer readable medium that bears computer usable instructions for one or more processors. The medium may be provided in various forms, including one or more diskettes, compact disks, tapes, chips, magnetic and electronic storage media, volatile memory, non-volatile memory and the like. Non-transitory computer-readable media may include all computer-readable media, with the exception being a transitory, propagating signal. The term non-transitory is not intended to exclude computer readable media such as primary memory, volatile memory, RAM and so on, where the data stored thereon may only be temporarily stored. The computer useable instructions may also be in various forms, including compiled and non-compiled code.

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing implementation of the various embodiments described herein.

The invention claimed is:

1. A system for real-time transmission of data streams comprising:
a video transmitting device comprising: at least one network interface and configured to generate and transmit via the at least one network interface at least: (i) a first data stream, the first data stream for providing to a browser and (ii) a second data stream, the first data stream and the second data stream generated based on a same captured video stream, the second data stream having a higher bitrate relative to the first data stream, the second data stream shifted in time relative to both the captured video stream and the first data stream;
a processor for communicating control signals to the video transmitting device, the processor configured to:
receive, from the browser, data representing at least one stream parameter;
generate electronic instructions based at least on the received data, the electronic instructions for causing modification of at least one generation or transmission factor associated with at least one of the first data stream or the second data stream based at least in part on the at least one stream parameter; and
communicate the electronic instructions to the video transmitting device,
the video transmitting device configured for receiving the electronic instructions and modifying the at least one generation or transmission factor in the generation or transmission of at least one of the first data stream or the second data stream;
wherein the modification of the at least one generation or transmission factor changes a bitrate of at least one of the first data stream or the second data stream thereby changing a utilization of transmission bandwidth shared between the transmission of first data stream and the transmission second data stream via the at least one network interface;
wherein the received data includes data associated with a number of frames transmitted and a number of acknowledgement indications, each of the acknowledgement indications provided when a frame is received at a destination;
wherein the processor is adapted to determine a difference between the number of acknowledgement indications and the number of frames transmitted; and wherein the electronic instructions, cause the video transmitting device to (i) decrease a transmission framerate if the difference between the number of acknowledgement indications and the number of frames transmitted is greater than X, and (ii) increase a transmission framerate if the difference between the number of acknowledgement indications and the number of frames transmitted is less than X; and
wherein X is an integer determined by a function of a moving average of the difference between the number of acknowledgement indications and the number of frames transmitted.

2. The system of claim 1, wherein the first data stream comprises a sequence of digital images encoded in an image file format, and each digital image of the sequence of digital images is temporally spaced out from one another.

3. The system of claim 1, wherein the second data stream comprises a full rate data stream including both (i) video data and (ii) audio data.

4. The system of claim 1, further comprising:
one or more transcoders adapted to transcode at least one of the first data stream or the second data stream received from the video transmitting device, and wherein the processor is further adapted to receive one or more transcoder performance feedback indications from the one or more transcoders; and the electronic instructions communicated to the video transmitting device are generated by the processor based at least in part on the one or more transcoder performance feedback indications.

5. The system of claim 4, wherein the processor is further adapted to generate a second set of electronic instructions to the one or more transcoders to cause the modification of one or more characteristics of the one or more transcoders, including at least one of (i) a number of transcoders operating in the one or more transcoders, or (ii) selecting at least one transcoder of the one or more transcoders to process a load.

6. The system of claim 4, wherein the one or more transcoder performance feedback indications include at least one of (i) performance indicators, (ii) computing load information, (iii) memory load information, or (iv) network parameters associated with at least one transcoder of the one or more transcoders.

7. The system of claim 1, wherein the one or more transmission quality factors include at least one of bandwidth, frame rate, bit rate, compression, resolution, color depth, encoding scheme, or modulation scheme.

8. The system of claim 1, wherein the first data stream is adapted for providing a low bandwidth preview for use with the browser and the second data stream is adapted for providing a high bandwidth signal for use with an end location configured for content distribution.

9. The system of claim 1, wherein the first data stream and the second data stream are transmitted simultaneously by the video transmitting device.

10. The system of claim 1, wherein at least one of the first data stream or the second data stream is transmitted over a bonded connection.

11. The system of claim 1, wherein the processor is adapted to receive control data from the browser and to transmit the control data to the video transmitting device to remotely control the video transmitting device.

12. The system of claim 1, wherein the received control data is received from a control room monitoring a plurality of video transmitting devices.

13. The system of claim 10, wherein the increase in transmission framerate or the decrease in transmission framerate is provided through sequentially increasing or decreasing steps.

14. The system of claim 10, wherein the increase in transmission framerate or the decrease in transmission framerate is provided through a continuous increasing or decreasing of the transmission framerate.

15. A device for communicating control signals to a video transmitting device adapted to generate and transmit at least: (i) a first data stream, the first data stream for providing to a browser and (ii) a second data stream, the first data stream and the second data stream generated based on a same captured video stream, the second data stream having a higher bitrate relative to the first data stream the second data stream shifted in time relative to both the captured video stream and the first data stream, the device comprising:
a processor configured to:
receive, from a browser, data representing at least one stream parameter;
generate electronic instructions based at least on the received data, the electronic instructions for causing modification of at least one generation or transmission factor associated with at least one of the first data stream or the second data stream based at least in part on the at least one stream parameter; and
communicate the electronic instructions to the video transmitting device, the video transmitting device configured for receiving the electronic instructions and modifying the at least one generation or transmission factor in the generation or transmission of at least one of the first data stream or the second data stream;
wherein the modification of the at least one generation or transmission factor changes a bitrate of at least one of the first data stream or the second data stream thereby changing a utilization of transmission bandwidth shared between the transmission of first data stream and the transmission second data stream;
wherein the received data includes data associated with a number of frames transmitted and a number of acknowledgement indications, each of the acknowledgement indications provided when a frame is received at a destination;
wherein the processor is adapted to determine a difference between the number of acknowledgement indications and the number of frames transmitted; and wherein the electronic instructions, cause the video transmitting device to (i) decrease a transmission framerate if the difference between the number of acknowledgement indications and the number of frames transmitted is greater than X, and (ii) increase a transmission framerate if the difference between the number of acknowledgement indications and the number of frames transmitted is less than X; and
wherein X is an integer determined by a function of a moving average of the difference between the number of acknowledgement indications and the number of frames transmitted.

16. The device of claim 15, wherein the processor is located in or proximate to the browser.

17. The device of claim 15, wherein the processor is located in or proximate to one or more transcoders.

18. The device of claim 15, wherein the processor is located in or proximate to the video transmitting device.

19. A computer-implemented method for real-time transmission of data streams from a video transmitting device adapted to generate and transmit at least: (i) a first data stream, the first data stream for providing to a browser and (ii) a second data stream, the first data stream and the second data stream generated based on the same captured video stream, the second data stream shifted in time relative to both the captured video stream and the first data stream, the second data stream having a higher bitrate relative to the first data stream, the method comprising:
receiving, from a browser, data representing at least one stream parameters;
generating, by a processor, electronic instructions based at least on the received data, the electronic instructions for causing modification of at least one generation or transmission factor associated with at least one of the first data stream or the second data stream based at least in part on the at least one stream parameter; and
communicating, by the processor, the electronic instructions to the video transmitting device, the video transmitting device configured for receiving the electronic instructions and modifying the at least one generation or transmission factor in the transmission of at least one of the first data stream or the second data stream;
wherein the modification of the at least one generation or transmission factor changes a bitrate of at least one of the first data stream or the second data stream thereby changing a utilization of transmission bandwidth shared between the transmission of first data stream and the transmission second data stream;
wherein the received data includes data associated with a number of frames transmitted and a number of acknowledgement indications, each of the acknowledgement indications provided when a frame is received at a destination;
wherein the processor is adapted to determine a difference between the number of acknowledgement indications and the number of frames transmitted; and wherein the electronic instructions, cause the video transmitting device to (i) decrease a transmission framerate if the difference between the number of acknowledgement indications and the number of frames transmitted is greater than X, and (ii) increase a transmission framerate if the difference between the number of acknowledgement indications and the number of frames transmitted is less than X; and wherein X is an integer determined by a function of a moving average of the difference between the number of acknowledgement indications and the number of frames transmitted.

20. The method of claim 19, wherein the first data stream comprises a sequence of digital images encoded in an image file format, and each digital image of the sequence of digital images is temporally spaced out from one another.

21. The method of claim 19, wherein the second data stream comprises a full rate data stream including both (i) video data and (ii) audio data.

22. The method of claim 19, further comprising:
receiving one or more transcoder performance feedback indications from one or more transcoders adapted to transcode data streams received from the video transmitting device; and
wherein the electronic instructions communicated to the video transmitting device are generated by the processor based at least in part on the one or more transcoder performance feedback indications.

23. The method of claim 22, further comprising:
generating a second set of electronic instructions to the one or more transcoders to cause the modification of one or more characteristics of the one or more transcoders, including at least one of (i) a number of transcoders operating in the one or more transcoders, or (ii) selecting at least one transcoder of the one or more transcoders to process a load.

24. The method of claim 19, wherein the increase in transmission framerate or the decrease in transmission framerate is provided through sequentially increasing or decreasing steps.

25. A non-transitory computer-readable media containing instructions, the instructions when executed on a processor coupled to a video transmitting device adapted to generate and transmit at least: (i) a first data stream, the first data stream for providing to a browser and (ii) a second data stream, the first data stream and the second data stream generated based on a same captured video stream, the second data stream having a higher bitrate relative to the first data stream, the second data stream shifted in time relative to both the captured video stream and the first data stream, cause the processor to perform the steps of:
receiving, from a browser, data representing at least one stream parameter;
generating electronic instructions based at least on the received data, the electronic instructions for causing modification of at least one generation or transmission factor associated with at least one of the first data stream or the second data stream based at least in part on the at least one stream parameter; and
communicating the electronic instructions to the video transmitting device, the video transmitting device configured for receiving the electronic instructions and modifying the at least one generation or transmission factor in the generation or transmission of at least one of the first data stream or the second data stream;
wherein the modification of the at least one generation or transmission factor changes a bitrate of at least one of the first data stream or the second data stream thereby changing a utilization of transmission bandwidth shared between the transmission of first data stream and the transmission second data stream;
wherein the received data includes data associated with a number of frames transmitted and a number of acknowledgement indications, each of the acknowledgement indications provided when a frame is received at a destination;
wherein the processor is adapted to determine a difference between the number of acknowledgement indications and the number of frames transmitted; and wherein the electronic instructions, cause the video transmitting device to (i) decrease a transmission framerate if the difference between the number of acknowledgement indications and the number of frames transmitted is greater than X, and (ii) increase a transmission framerate if the difference between the number of acknowledgement indications and the number of frames transmitted is less than X; and
wherein X is an integer determined by a function of a moving average of the difference between the number of acknowledgement indications and the number of frames transmitted.

26. The non-transitory computer-readable media of claim 25, wherein the instructions when executed on a processor cause the processor to further perform the steps of:
receiving one or more transcoder performance feedback indications from one or more transcoders adapted to transcode data streams received from the video transmitting device;
wherein the electronic instructions communicated to the video transmitting device are generated by the processor based at least in part on the one or more transcoder performance feedback indications; and
generating a second set of electronic instructions to the one or more transcoders to cause the modification of one or more characteristics of the one or more transcoders, including at least one of (i) a number of transcoders operating in the one or more transcoders, or (ii) load balancing as between individual transcoders of the one or more transcoders.

27. The system of claim 1, wherein the at least one stream parameter includes at least one parameter from the group consisting of: a framerate, a resolution, and a data rate.

28. The system of claim 1, wherein the moving average is an exponential moving average.

29. The system of claim 28, wherein X is approximately 1.25*the exponential moving average of the difference.

30. The system of claim 28, wherein a smoothing value of the exponential moving average is based on one or more characteristics of the transmission via the at least one network interface.

* * * * *